United States Patent
Weber et al.

(12) 
(10) Patent No.: US 6,350,875 B1
(45) Date of Patent: Feb. 26, 2002

(54) SYNTHESIS OF CYCLOOCTATETRAENE DERIVATIVES AND THEIR USE AS ELECTRON TRANSPORTERS IN ORGANIC LIGHT EMITTING DIODES

(75) Inventors: William P. Weber; Ping Lu, both of Los Angeles; Mark E. Thompson, Anaheim; Haiping Hong, Los Angeles, all of CA (US)

(73) Assignee: The University of Southern California, Los Angeles, CA (US)

( * ) Notice: Subject to any disclaimer, the term of this patent is extended or adjusted under 35 U.S.C. 154(b) by 0 days.

(21) Appl. No.: 09/816,527

(22) Filed: Mar. 23, 2001

Related U.S. Application Data

(63) Continuation of application No. 09/375,126, filed on Aug. 16, 1999, now abandoned.

(51) Int. Cl.$^7$ .............................................. C07D 215/04
(52) U.S. Cl. ....................... 546/173; 546/255; 546/256; 549/15; 549/23; 549/49; 549/59; 558/44; 568/331; 568/631; 570/127; 570/183
(58) Field of Search ................................. 546/173, 256, 546/255; 549/23, 15, 49, 59; 558/44; 568/331, 631; 570/127, 183

(56) References Cited

U.S. PATENT DOCUMENTS

| | | |
|---|---|---|
| 5,703,436 A | 12/1997 | Forrest et al. |
| 5,707,745 A | 1/1998 | Forrest et al. |
| 5,757,026 A | 5/1998 | Forrest et al. |
| 5,757,139 A | 5/1998 | Forrest et al. |
| 5,811,833 A | 9/1998 | Thompson |
| 5,834,893 A | 11/1998 | Bulovic et al. |
| 5,844,363 A | 12/1998 | Gu et al. |
| 5,861,219 A | 1/1999 | Thompson et al. |
| 5,874,803 A | 2/1999 | Garbuzov et al. |
| 5,917,280 A | 6/1999 | Burrows et al. |
| 5,932,895 A | 8/1999 | Shen et al. |
| 5,986,401 A | 11/1999 | Thompson et al. |
| 6,013,982 A | 1/2000 | Thompson et al. |
| 6,045,930 A | 4/2000 | Thompson et al. |
| 6,046,543 A | 4/2000 | Bulovic et al. |
| 6,048,630 A | 4/2000 | Burrows et al. |
| 6,091,195 A | 7/2000 | Forrest et al. |
| 6,111,902 A | 8/2000 | Kozlov et al. |
| 6,125,226 A | 9/2000 | Forrest et al. |

FOREIGN PATENT DOCUMENTS

| | | |
|---|---|---|
| JP | 60-217213 | 10/1985 |
| JP | 61-43149 | 3/1986 |
| WO | 96/19792 | 6/1996 |
| WO | 97/33296 | 9/1997 |
| WO | 97/48115 | 12/1997 |
| WO | 97/48139 | 12/1997 |
| WO | 98/50989 | 11/1998 |

OTHER PUBLICATIONS

CA 77:62126, abstract of Recl Trav Chim Pays–Bas, 1972, 91(5), 667–670.*
C.W. Tang, et al., "Organic Electroluminescent Diodes", 51 *Appl. Phys. Lett.,* 913 (1987).
S.R. Forrest, et al., "Organic Emitters Promise a New Generation of Displays", *Laser Focus World,* (Feb. 1995).
Baldo, et al., "Very high efficiency green organic light–emitting devices based on electrophosphorescence", 75 *Applied Physics Letters,* 4–6, (1999).
C.H. Chen, et al., "Recent developments in molecular organic electroluminescent materials", *Macromolecular Symposia,* 125, 1–48 (1997).
M.A. Baldo, et al., "Highly efficient phosphorescent emission from organic electroluminescent devices", *Nature,* vol. 395, 151–154, (Sep. 1998).
H. Aziz, et al., "Degradation Mechanism of Small Molecule–Based Organic Light–Emitting Devices", *Science,* 283, 1900–1902 (Mar. 19, 1999).
A.C. Cope, et al., "Substituted Cyclooctatraenes from Substituted Acetylenes", *J. Am. Chem. Soc.,* 73, 3536 (1951).
C.W. Tang, et al., "Electroluminescence of doped organic films," 65 *J. Appl. Phys.,* 3610–3616, (1989).
V. Bulovic, et al., "Bright, saturated, red–to–yellow organic light–emitting devices based on polarization–induced spectral shifts," *Chem. Phys. Lett.,* 287, 455–460 (1998).
H.J.A. Dartnall, et al., 220 *Proc. Roy. Soc. B* (London), 115–130 (1983).
H. Guo, et al., "Synthesis of High Molecular Weight Copolymers by Ruthenium–Catalyzed Step–Growth Copolymerization of Acetophenone with $\alpha,\omega$–Dienes", *Macromolecules,* 28, 5686–5687 (1995).
G. Schröder, *Cyclooctatetraenes,* Verlag–Chemie GmbH, Weinheim, Germany (1965).
F.A.L. Anet, et al., "Ring Inversion and Bond Shift in Cyclooctatetraene Derivatives", *J. Am. Chem. Soc.,* 86, 3576 (1964).
J.R. Leto, et al., "Tetrasubstituted Cyclooctatetraenes: Catalytic Cyclotetramerization of Propiolic Acid Esters with Tetrakis–(phosphorus trihalide)–Nickel(0) Complexes", *J. Am. Chem. Soc.,* 83, 2944 (1961).
J.I. Levison, et al., "Transition–metal Complexes containing Phosphorus Ligands. Part III. Convenient Syntheses of Some Triphenylphosphine Complexes of the Platinum Metals", *J. Chem. Soc., A.,* 2947 (1970).
A. Vogel, *Vogel's Textbook of Practical Organic Chemistry,* 4$^{th}$ Ed., Longman, London, England, p. 351 (1978).

(List continued on next page.)

*Primary Examiner*—D. Margaret Seaman
(74) *Attorney, Agent, or Firm*—Kenyon & Kenyon

(57) ABSTRACT

The synthesis of asymmetric tetrasubstituted cyclooctatetraenes ("COTs") and the use of said compounds in organic light emitting diodes is reported, wherein said COTs represent a class of wide gap electron transporters that are readily deposited in vacuum.

27 Claims, 20 Drawing Sheets

OTHER PUBLICATIONS

Figure 1:
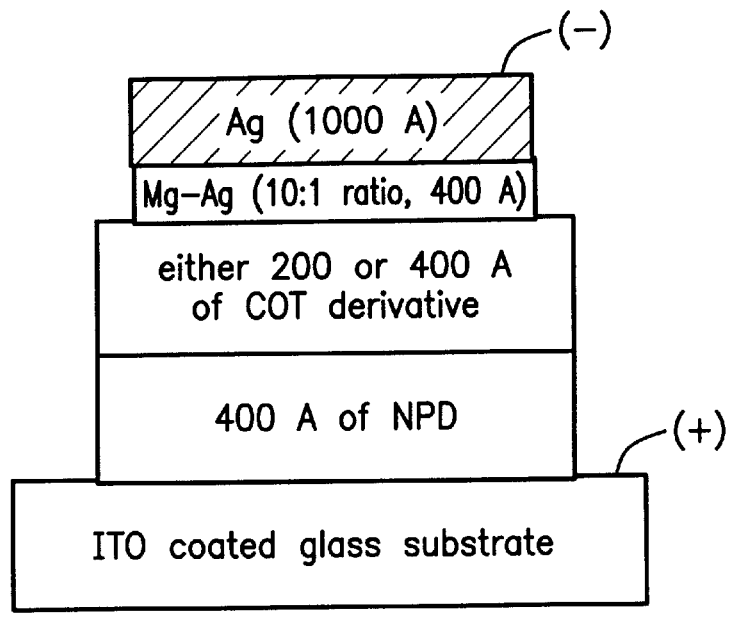
Figure 1:
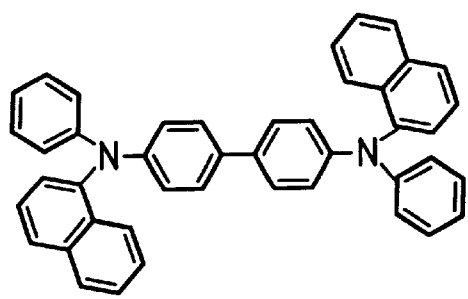
Figure 2A:
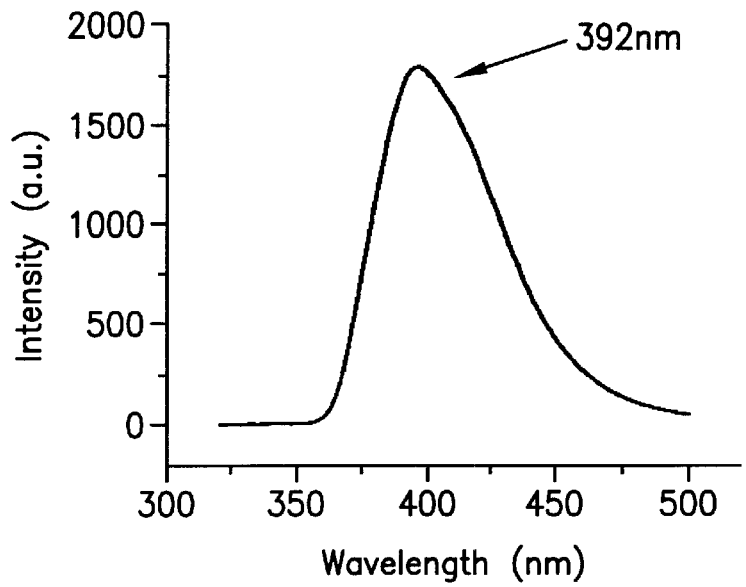
Figure 2A:
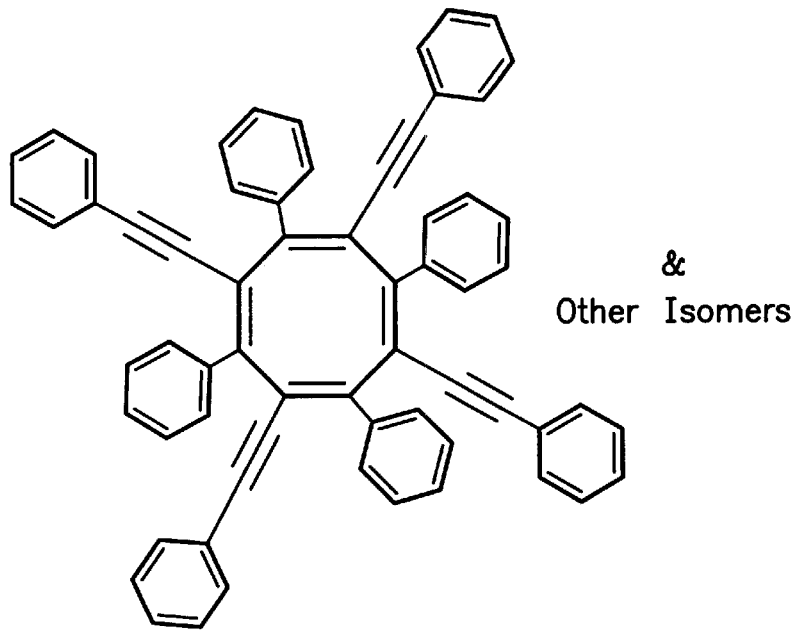
Figure 2B:
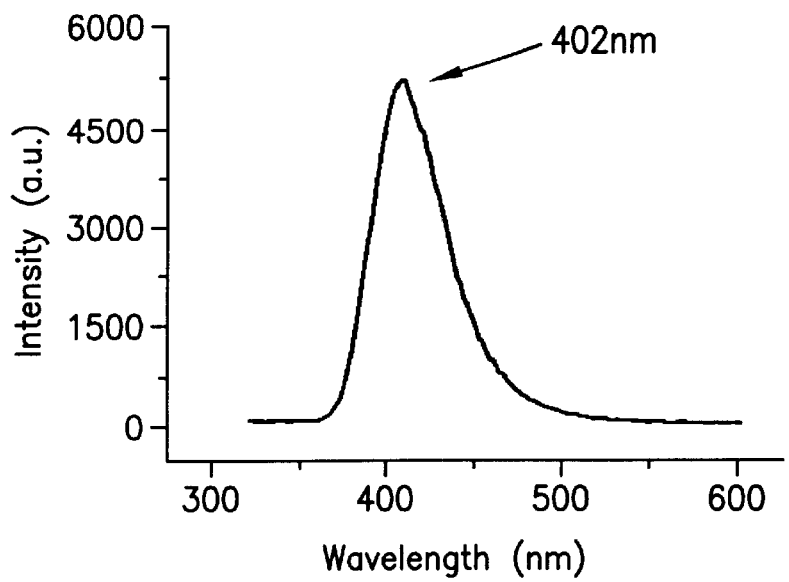
Figure 2B:
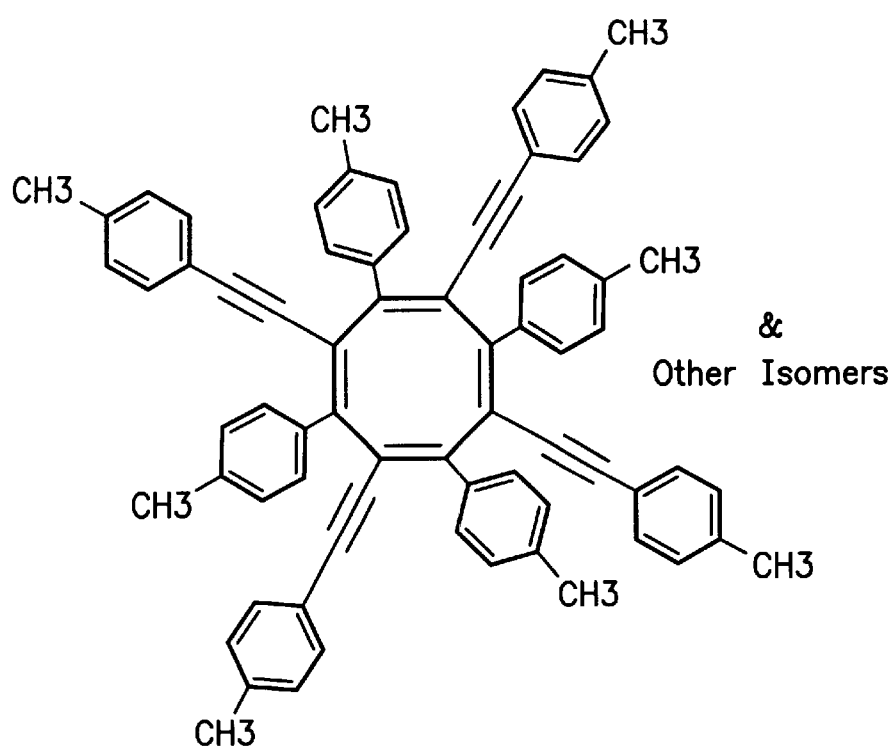

M. Cariou, "Anodic Oxidation of Diarylacetylenes and Diaryldiacetylenes: Electrosynthesis of Diaroyl–Stilbenes and Acetylenic α– and γ–Diketones", *Tetrahedron*, 47(4/5), 799 (1991).

A. Sarkar, et al., "A Convenient Synthesis of Aromatic–Ring Substituted Diacetylenes", *Helv. Chim. Acta.*, 82, 138 (1999).

S.R. Forrest, "Ultrathin Organic Films Grown by Organic Molecular Beam Deposition and Related Techniques," Chemical Reviews, 1997, 97, pp. 1793–1896.

A.E. Van der Hout–Lodder, et al., "Regiospecific two–step conversion of a diaryl–substituted acetylene into an octaarylcyclooctatetraene", Chemical Abstracts 77:62126, abstract of Recl Trav Chim Pays–Bas, 1972, 91(5), 667–670.

* cited by examiner

HTL (NPD)

COT = substituted cyclooctateraene

Photoluminescence of COT-H

Chemical Structure of CoT-H

& Other Isomers

Photoluminescence of COT-Me

Chemical Structure of CoT-Me

& Other Isomers

OLED: NPD (400A)/COT-Me (400A)

OLED: NPD (400A)/COT-H (400A)

OLED: NPD (400A)/COT-Me (200A)

SYNTHESIS OF CYCLOOCTATETRAENE DERIVATIVES AND THEIR USE AS ELECTRON TRANSPORTERS IN ORGANIC LIGHT EMITTING DIODES

CROSS-REFERENCE TO RELATED APPLICATION

This application is a continuation of U.S. Ser. No. 09/375,126, filed Aug. 16, 1999 now abandoned.

I. FIELD OF INVENTION

The present invention is directed to the synthesis of novel cyclooctatetraene derivatives and their use in organic light emitting devices (OLEDs) comprising an electron transporting layer ("ETL") comprising said derivatives of cyclooctatetraene.

II. BACKGROUND OF THE INVENTION

II. A. General Background

Organic light emitting devices (OLEDs) are comprised of several organic layers in which one of the layers is comprised of an organic material that can be made to electroluminesce by applying a voltage across the device, C. W. Tang et al., Appl. Phys. Lett. 1987, 51, 913. Certain OLEDs have been shown to have sufficient brightness, range of color and operating lifetimes for use as a practical alternative technology to LCD-based full color flat-panel displays (S. R. Forrest, P. E. Burrows and M. E. Thompson, Laser Focus World, February 1995). Since many of the thin organic films used in such devices are transparent in the visible spectral region, they allow for the realization of a completely new type of display pixel in which red (R), green (G), and blue (B) emitting OLEDs are placed in a vertically stacked geometry to provide a simple fabrication process, a small R-G-B pixel size, and a large fill factor, International Patent Application No. PCT/US95/15790.

A transparent OLED (TOLED), which represents a significant step toward realizing high resolution, independently addressable stacked R-G-B pixels, was reported in International Patent Application No. PCT/US97/02681 in which the TOLED had greater than 71% transparency when turned off and emitted light from both top and bottom device surfaces with high efficiency (approaching 1% quantum efficiency) when the device was turned on. The TOLED used transparent indium tin oxide (ITO) as the hole-injecting electrode and a Mg—Ag-ITO electrode layer for electron-injection. A device was disclosed in which the ITO side of the Mg—Ag-ITO layer was used as a hole-injecting contact for a second, different color-emitting OLED stacked on top of the TOLED. Each layer in the stacked OLED (SOLED) was independently addressable and emitted its own characteristic color. This colored emission could be transmitted through the adjacently stacked, transparent, independently addressable, organic layer or layers, the transparent contacts and the glass substrate, thus allowing the device to emit any color that could be produced by varying the relative output of the red and blue color-emitting layers.

PCT/US95/15790 application disclosed an integrated SOLED for which both intensity and color could be independently varied and controlled with external power supplies in a color tunable display device. The PCT/US95/15790 application, thus, illustrates a principle for achieving integrated, full color pixels that provide high image resolution, which is made possible by the compact pixel size. Furthermore, relatively low cost fabrication techniques, as compared with prior art methods, may be utilized for making such devices.

II.B. Background of Emission

II.B.1. Basics

II.B. 1.a. Singlet and Triplet Excitons

Because light is generated in organic materials from the decay of molecular excited states or excitons, understanding their properties and interactions is crucial to the design of efficient light emitting devices currently of significant interest due to their potential uses in displays, lasers, and other illumination applications. For example, if the symmetry of an exciton is different from that of the ground state, then the radiative relaxation of the exciton is disallowed and luminescence will be slow and inefficient. Because the ground state is usually anti-symmetric under exchange of spins of electrons comprising the exciton, the decay of a symmetric exciton breaks symmetry. Such excitons are known as triplets, the term reflecting the degeneracy of the state. For every three triplet excitons that are formed by electrical excitation in an OLED, only one symmetric state (or singlet) exciton is created. (M. A. Baldo, D. F. O'Brien, M. E. Thompson and S. R. Forrest, Very high-efficiency green organic light-emitting devices based on electrophosphorescence, Applied Physics Letters, 1999, 75, 4–6.) Luminescence from a symmetry-disallowed process is known as phosphorescence. Characteristically, phosphorescence may persist for up to several seconds after excitation due to the low probability of the transition. In contrast, fluorescence originates in the rapid decay of a singlet exciton. Since this process occurs between states of like symmetry, it may be very efficient.

Many organic materials exhibit fluorescence from singlet excitons. However, only a very few have been identified which are also capable of efficient room temperature phosphorescence from triplets. Thus, in most fluorescent dyes, the energy contained in the triplet states is wasted. However, if the triplet excited state is perturbed, for example, through spin-orbit coupling (typically introduced by the presence of a heavy metal atom), then efficient phosphoresence is more likely. In this case, the triplet exciton assumes some singlet character and it has a higher probability of radiative decay to the ground state. Indeed, phosphorescent dyes with these properties have demonstrated high efficiency electroluminescence.

Only a few organic materials have been identified which show efficient room temperature phosphorescence from triplets. In contrast, many fluorescent dyes are known (C. H. Chen, J. Shi, and C. W. Tang, "Recent developments in molecular organic electroluminescent materials," Macromolecular Symposia, 1997, 125, 1–48; U. Brackmann, Lambdachrome Laser Dyes (Lambda Physik, Gottingen, 1997) and fluorescent efficiencies in solution approaching 100% are not uncommon. (C. H. Chen, 1997, op. cit.) Fluorescence is also not affected by triplet-triplet annihilation, which degrades phosphorescent emission at high excitation densities. (M. A. Baldo, et al., "High efficiency phosphorescent emission from organic electroluminescent devices," Nature, 1998, 395, 151–154; M. A. Baldo, M. E. Thompson, and S. R. Forrest, "An analytic model of triplet-triplet annihilation in electrophosphorescent devices," 1999). Consequently, fluorescent materials are suited to many electroluminescent applications, particularly passive matrix displays.

II.B.1.b. Overview of invention relative to basics

This invention pertains to the use of cyclooctatetraene derivatives to enhance the performance of organic light emitting devices ("OLEDs").

A great deal of work has been done to optimize OLEDs. The materials for the hole transporting layer have been extensively engineered to achieve maximum efficiency and lifetime for the devices. However, the best devices to date are still made with the same electron transporting material that was reported in the seminal paper by Tang and Van Slyke, Appl. Phys. Lett. 1987, 51, 913. which material is tris-(8-hydroxyquinoline) aluminum ("Alq3"). While Alq3 has a good electron mobility and gives OLEDs with long lifetimes, it is chemically unstable and hole injection into the material appears to lead to degradation of the Alq3 (H. Aziz, Z. D. Popovic, et al., Science, 283, 1900–1902 (Mar. 19, 1999)). Other materials have been explored as ETLs, but none has proven to be as effective as Alq3.

A family of cyclooctatetraenes (COTs) has been prepared and tested as electron transporting agents in OLEDs. The goal here is to replace the Alq3 ETL of conventional OLEDs with a different, better material. The COT derivatives have a high energy gap, emitting in the blue to violet region of the visible spectrum and are very thermally stable (the glass transition temperature, Tg, >150° C.). They have low volatility, making them ideal for vacuum deposition and they form stable glassy films. They are hydrolytically stable and they are compatible with a wide range of substrates and materials. Prior to this work it was not known if these materials would transport holes or electrons in optoelectronic devices.

In one embodiment of the present invention, we present the use of dihydridocarbonyltris(triphenylphosphine) ruthenium, which has been activated by treatment with a stoichiometric amount of styrene, as a catalyst to form the tetramer of respectively diphenylbutadiyne, di-p-tolylbutadiyne, di-p-methoxyphenylbutadiyne, bis-(β-naphthyl)-1,4-butadiyne, bis(3-thienyl)-1,4-butadiyne, and bis-(4-trifluoromethylphenyl)-1,4-butadiyne.

In a second embodiment of the present invention, we focus on the use of this catalyst with diphenylacetylene. Under identical conditions to the first embodiment, the product is 75% 1,2,3 triphenyl naphthalene (instead of expected octa phenyl COT; octa aryl COT are made using conventional catalysts such as Ni (A. C. Cope, H. C. Campbell, J. Am. Chem. Soc., 1951, 71, 3536); the octa (meta or ortho) tolyl COT derivative is of interest because we expect it to be a more thermally stable glass based on steric reasons.

In a third embodiment of the present invention, we note that mixtures of alkyne monomers may be used to make tetramers.

In a fourth embodiment of the present invention, we note that cyclic voltammetry of the tetramers (including H-COT and Me-COT) allows measurement of the energy of the lowest unoccupied molecular orbital ("LUMO") (which gives an estimate of energy of injected electron in COT material) which allows systematic prediction of optimum devices. The reduction potential of a compound measured by cyclic voltammetry correlates with the LUMO energy of the compound; knowledge of the LUMO of a given COT derivative allows one of ordinary skill to select appropriate, optimum components for use in an OLED. [Reduction potentials herein are reported with respect to the saturated calomel electrode (SCE).]

In a fifth embodiment of this invention, we describe the use of certain COT derivatives in functioning OLEDs.

These embodiments are discussed in more detail in the examples below. However the embodiments may operate by different mechanisms. Without limiting the scope of the invention, we discuss the different mechanisms.

II.B.1.c. Dexter and Förster mechanisms

To understand the different embodiments of this invention it is useful to discuss the underlying mechanistic theory of energy transfer. There are two mechanisms commonly discussed for the transfer of energy to an acceptor molecule. In the first mechanism of Dexter transport (D. L. Dexter, "A theory of sensitized luminescence in solids," J. Chem. Phys., 1953, 21, 836–850), the exciton may hop directly from one molecule to the next. This is a short-range process dependent on the overlap of molecular orbitals of neighboring molecules. It also preserves the symmetry of the donor and acceptor pair (E. Wigner and E. W. Wittmer, Uber die Struktur der zweiatomigen Molekelspektren nach der Quantenmechanik, Zeitschrift fur Physik, 1928, 51, 859–886; M. Klessinger and J. Michl, Excited states and photochemistry of organic molecules (VCH Publishers, New York, 1995). Thus, the energy transfer of Eq. (1) is not possible via Dexter mechanism. In the second mechanism of Förster transfer (T. Förster, Zwischenmolekulare Energiewanderung and Fluoreszenz, Annalen der Physik, 1948, 2, 55–75; T. Förster, Fluoreszenz organischer Verbindugen (Vandenhoek and Ruprecht, Gottinghen, 1951), the energy transfer of Eq. (1) is possible. In Förster transfer, similar to a transmitter and an antenna, dipoles on the donor and acceptor molecules couple and energy may be transferred. Dipoles are generated from allowed transitions in both donor and acceptor molecules. This typically restricts the Förster mechanism to transfers between singlet states.

Nevertheless, as long as the phosphor can emit light due to some perturbation of the state such as due to spin-orbit coupling introduced by a heavy metal atom, it may participate as the donor in Förster transfer. The efficiency of the process is determined by the luminescent efficiency of the phosphor (F Wilkinson, in Advances in Photochemistry (eds. W. A. Noyes, G. Hammond, and J. N. Pitts, pp. 241–268, John Wiley & Sons, New York, 1964), i.e. if a radiative transition is more probable than a non-radiative decay, then energy transfer will be efficient. Such triplet-singlet transfers were predicted by Förster (T. Förster,"Transfer mechanisms of electronic excitation," Discussions of the Faraday Society, 1959, 27, 7–17) and confirmed by Ermolaev and Sveshnikova (V. L. Ermolaev and E. B. Sveshnikova, "Inductive-resonance transfer of energy from aromatic molecules in the triplet state," Doklady Akademii Nauk SSSR, 1963, 149, 1295–1298), who detected the energy transfer using a range of phosphorescent donors and fluorescent acceptors in rigid media at 77K or 90K. Large transfer distances are observed; for example, with triphenylamine as the donor and chrysoidine as the acceptor, the interaction range is 52Å.

The remaining condition for Förster transfer is that the absorption spectrum should overlap the emission spectrum of the donor assuming the energy levels between the excited and ground state molecular pair are in resonance. In Example 1 of this application, we use the green phosphor fac tris(2-phenylpyridine) iridium (Ir(ppy)$_3$; M. A. Baldo, et al., Appl. Phys. Lett., 1999, 75, 4–6) and the red fluorescent dye [2-methyl-6-[2-(2,3,6,7-tetrahydro-1H,5H-benzo[ij] quinolizin-9-yl) ethenyl]-4H-pyran-ylidene] propane-dinitrile]("DCM2"; C. W. Tang, S. A. VanSlyke, and C. H. Chen, "Electroluminescence of doped organic films," J. Appl. Phys., 1989, 65, 3610–3616). DCM2 absorbs in the green, and, depending on the local polarization field (V. Bulovic, et al., "Bright, saturated, red-to-yellow organic light-emitting devices based on polarization-induced spectral shifts," Chem. Phys. Lett., 1998, 287, 455–460), it emits at wavelengths between λ=570 nm and λ=650 nm.

It is possible to implement Förster energy transfer from a triplet state by doping a fluorescent guest into a phosphorescent host material. Unfortunately, such systems are affected by competitive energy transfer mechanisms that degrade the overall efficiency. In particular, the close proximity of the host and guest increase the likelihood of Dexter transfer between the host to the guest triplets. Once excitons reach the guest triplet state, they are effectively lost since these fluorescent dyes typically exhibit extremely inefficient phosphorescence.

To maximize the transfer of host triplets to fluorescent dye singlets, it is desirable to maximize Dexter transfer into the triplet state of the phosphor while also minimizing transfer into the triplet state of the fluorescent dye. Since the Dexter mechanism transfers energy between neighboring molecules, reducing the concentration of the fluorescent dye decreases the probability of triplet-triplet transfer to the dye. On the other hand, long range Förster transfer to the singlet state is unaffected. In contrast, transfer into the triplet state of the phosphor is necessary to harness host triplets, and may be improved by increasing the concentration of the phosphor.

II.B.2. Interrelation of device structure and emission

Devices whose structure is based upon the use of layers of organic optoelectronic materials generally rely on a common mechanism leading to optical emission. Typically, this mechanism is based upon the radiative recombination of a trapped charge. Specifically, OLEDs are comprised of at least two thin organic layers separating the anode and cathode of the device. The material of one of these layers is specifically chosen based on the material's ability to transport holes, a "hole transporting layer" (HTL), and the material of the other layer is specifically selected according to its ability to transport electrons, an "electron transporting layer" (ETL). With such a construction, the device can be viewed as a diode with a forward bias when the potential applied to the anode is higher than the potential applied to the cathode. Under these bias conditions, the anode injects holes (positive charge carriers) into the hole transporting layer, while the cathode injects electrons into the electron transporting layer. The portion of the luminescent medium adjacent to the anode thus forms a hole injecting and transporting zone while the portion of the luminescent medium adjacent to the cathode forms an electron injecting and transporting zone. The injected holes and electrons each migrate toward the oppositely charged electrode. When an electron and hole localize on the same molecule, a Frenkel exciton is formed. Recombination of this short-lived state may be visualized as an electron dropping from its conduction potential to a valence band, with relaxation occurring, under certain conditions, preferentially via a photoemissive mechanism. Under this view of the mechanism of operation of typical thin-layer organic devices, the electroluminescent layer comprises a luminescence zone receiving mobile charge carriers (electrons and holes) from each electrode.

As noted above, light emission from OLEDs is typically via fluorescence or phosphorescence. There are issues with the use of phosphore-cence. It has been noted that phosphorescent efficiency can decrease rapidly at high current densities. It may be that long phosphorescent lifetimes cause saturation of emissive sites, and triplet-triplet annihilation may also produce efficiency losses. Another difference between fluorescence and phosphorescence is that energy transfer of triplets from a conductive host to a luminescent guest molecule is typically slower than that of singlets; the long range dipole-dipole coupling (Förster transfer) which dominates energy transfer of singlets is (theoretically) forbidden for triplets by the principle of spin symmetry conservation. Thus, for triplets, energy transfer typically occurs by diffusion of excitons to neighboring molecules (Dexter transfer); significant overlap of donor and acceptor excitonic wavefunctions is critical to energy transfer. Another issue is that triplet diffusion lengths are typically long (e.g., >1400 Å) compared with typical singlet diffusion lengths of about 200 Å. Thus, if phosphorescent devices are to achieve their potential, device structures need to be optimized for triplet properties. In this invention, we exploit the property of long triplet diffusion lengths to improve external quantum efficiency.

Successful utilization of phosphorescence holds enormous promise for organic electroluminescent devices. For example, an advantage of phosphorescence is that all excitons (formed by the recombination of holes and electrons in an EL), which are (in part) triplet-based in phosphorescent devices, may participate in energy transfer and luminescence in certain electroluminescent materials. In contrast, only a small percentage of excitons in fluorescent devices, which are singlet-based, result in fluorescent luminescence.

An alternative is to use phosphorescence processes to improve the efficiency of fluorescence processes. Fluorescence is in principle 75% less efficient due the three times higher number of symmetric excited states.

II.C. Background of Materials

II.C.1. Basic heterostructures

Because one typically has at least one electron transporting layer and at least one hole transporting layer, one has layers of different materials, forming a heterostructure. The materials that produce the electroluminescent emission may be the same materials that function either as the electron transporting layer or as the hole transporting layer. Such devices in which the electron transporting layer or the hole transporting layer also functions as the emissive layer are referred to as having a single heterostructure. Alternatively, the electroluminescent material may be present in a separate emissive layer between the hole transporting layer and the electron transporting layer in what is referred to as a double heterostructure. The separate emissive layer may contain the emissive molecule doped into a host or the emissive layer may consist essentially of the emissive molecule.

That is, in addition to emissive materials that are present as the predominant component in the charge carrier layer, that is, either in the hole transporting layer or in the electron transporting layer, and that function both as the charge carrier material as well as the emissive material, the emissive material may be present in relatively low concentrations as a dopant in the charge carrier layer. Whenever a dopant is present, the predominant material in the charge carrier layer may be referred to as a host compound or as a receiving compound. Materials that are present as host and dopant are selected so as to have a high level of energy transfer from the host to the dopant material. In addition, these materials need to be capable of producing acceptable electrical properties for the OLED. Furthermore, such host and dopant materials are preferably capable of being incorporated into the OLED using materials that can be readily incorporated into the OLED by using convenient fabrication techniques, in particular, by using vacuum-deposition techniques.

II.C.2. Exciton blocking layer

One can have an exciton blocking layer in OLED devices to substantially block the diffusion of excitons, thus substantially keeping the excitons within the emission layer to enhance device efficiency. The material of blocking layer is characterized by an energy difference ("band gap") between its lowest unoccupied molecular orbital (LUMO) and its highest occupied molecular orbital (HOMO) This band gap substantially prevents the diffusion of excitons through the blocking layer, yet has only a minimal effect on the turn-on voltage of a completed electroluminescent device. The band gap is thus preferably greater than the energy level of excitons produced in an emission layer, such that such excitons are not able to exist in the blocking layer. Specifically, the band gap of the blocking layer is at least as great as the difference in energy between the triplet state and the ground state of the host.

For a situation with a blocking layer between a hole-conducting host and the electron transporting layer, one seeks the following characteristics, which are listed in order of relative importance.

1. The difference in energy between the LUMO and HOMO of the blocking layer is greater than the difference in energy between the triplet and ground state singlet of the host material.
2. Triplets in the host material are not quenched by the blocking layer.
3. The ionization potential (IP) of the blocking layer is greater than the ionization potential of the host. (Meaning that holes are held in the host.)
4. The energy level of the LUMO of the blocking layer and the energy level of the LUMO of the host are sufficiently close in energy such that there is less than 50% change in the overall conductivity of the device.
5. The blocking layer is as thin as possible subject to having a thickness of the layer that is sufficient to effectively block the transport of excitons from the emissive layer into the adjacent layer.

That is, to block excitons and holes, the ionization potential of the blocking layer should be greater than that of the HTL, while the electron affinity of the blocking layer should be approximately equal to that of the ETL to allow for facile transport of electrons.

[For a situation in which the emissive ("emitting") molecule is used without a hole transporting host, the above rules for selection of the blocking layer are modified by replacement of the word "host" by "emitting molecule."]

For the complementary situation with a blocking layer between a electronconducting host and the hole-transporting layer one seeks characteristics (listed in order of importance):

1. The difference in energy between the LUMO and HOMO of the blocking layer is greater than the difference in energy between the triplet and ground state singlet of the host material.
2. Triplets in the host material are not quenched by the blocking layer.
3. The energy of the LUMO of the blocking layer is greater than the energy of the LUMO of the (electron-transporting) host. (Meaning that electrons are held in the host.)
4. The ionization potential of the blocking layer and the ionization potential of the host are such that holes are readily injected from the blocker into the host and there is less than a 50% change in the overall conductivity of the device.
5. The blocking layer is as thin as possible subject to having a thickness of the layer that is sufficient to effectively block the transport of excitons from the emissive layer into the adjacent layer.

[For a situation in which the emissive ("emitting") molecule is used without an electron transporting host, the above rules for selection of the blocking layer are modified by replacement of the word "host" by "emitting molecule."]

II.D. Color

As to colors, it is desirable for OLEDs to be fabricated using materials that provide electroluminescent emission in a relatively narrow band centered rear selected spectral regions, which correspond to one of the three primary colors, red, green and blue so that they may be used as a colored layer in an OLED or SOLED. It is also desirable that such compounds be capable of being readily deposited as a thin layer using vacuum deposition techniques so that they may be readily incorporated into an OLED that is prepared entirely from vacuum-deposited organic materials.

U.S. Ser. No. 08/774,333, filed Dec. 23, 1996, is directed to OLEDs containing emitting compounds that produce a saturated red emission.

III. SUMMARY OF THE INVENTION

At the most general level, the present invention is directed to the synthesis of certain cyclooctatetraene ("COT") molecules and to the use of said COT molecules in organic light emitting devices comprising an electron transporting layer comprising derivatives of cyclooctatetraene ("COTs") and an emissive layer wherein the emissive layer comprises an emissive molecule, which molecule is adapted to luminesce when a voltage is applied across a heterostructure. The COTs represent a new class of wide gap electron transporters that are readily deposited in vacuum. They an be synthesized in good yield (>75% isolated yields) from commercially available starting materials.

This invention is to directed to a cyclooctatetraene molecule of the formula

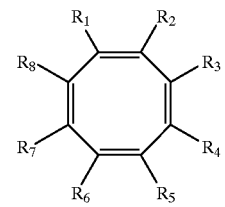

wherein $R_1$ through $R_8$ are selected from the group consisting of alkyl, aryl and alkynyl and wherein at least one member of $R_1$ through $R_8$ is different from the other members of $R_1$ through wherein at least one member of $R_1$ through $R_8$ is different from the other members of $R_1$ through $R_8$.

Of the synthesis, dihydridocarbonyltris (triphenylphosphine) ruthenium which has been activated by treatment with a stoichiometric amount of styrene catalyzes the cyclotetramerization of diphenylbutadiyne to give the unsymmetrical 1,2,4,6-tetraphenyl -3,5,7,8- tetrakis (phenylethynyl) cyclooctatetraene in high yield. The reaction can also be used with substituted phenylbutadiynes to yield (phenylethynyl) cyclooctatetracnes.

In a first embodiment of the use of these cyclooctatetraenes in OLEDs, a member of the class of cyclooctatetraenes is used to form an electron transporting layer in an OLED wherein the hole transporting layer comprises the emissive molecule of the device.

In a second embodiment in OLEDs, a member of the class of cyclooctatetraenes is used to form an electron transporting layer in an OLED to enhance the emission of a molecule in the hole transporting layer.

IV. BRIEF DESCRIPTION OF THE DRAWINGS

FIG. 1. OLED structure.

FIG. 2. Structure of COT derivatives and their luminescent spectra.

Figure 3:
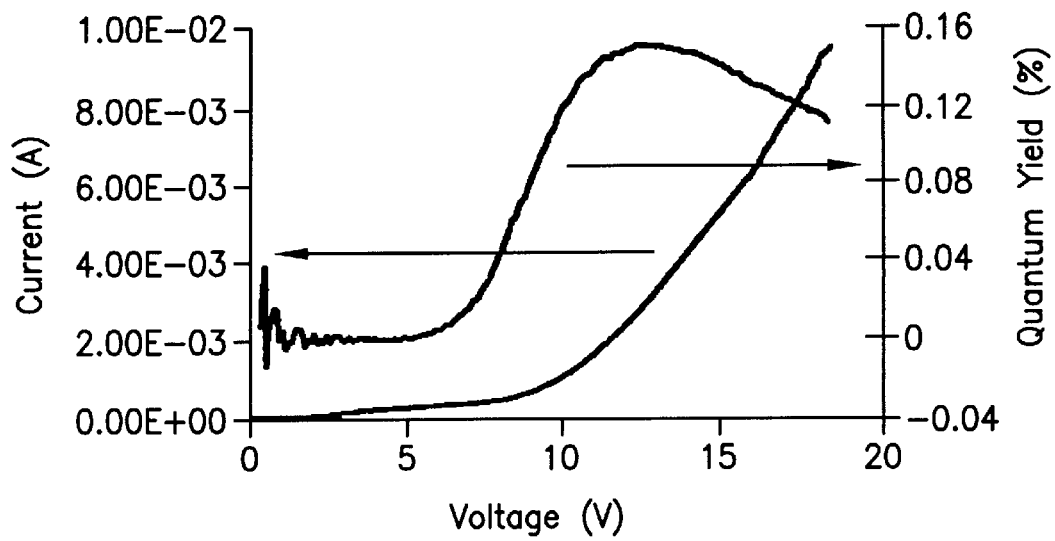
Figure 3:
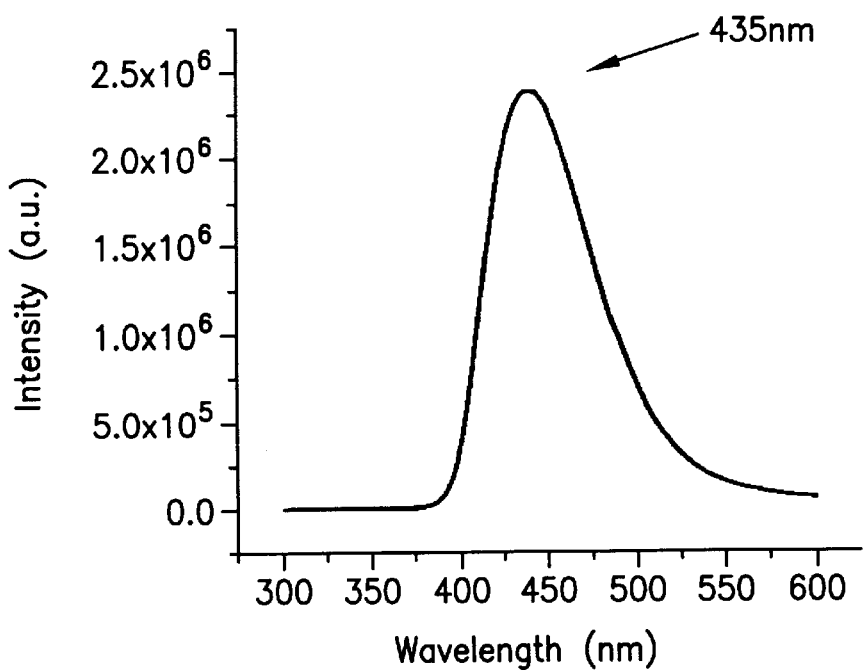

FIG. 3. IV characteristics, Q.E./V and EL spectra of OLED fabricated with a 400 Å COT-Me layer.

Figure 4:
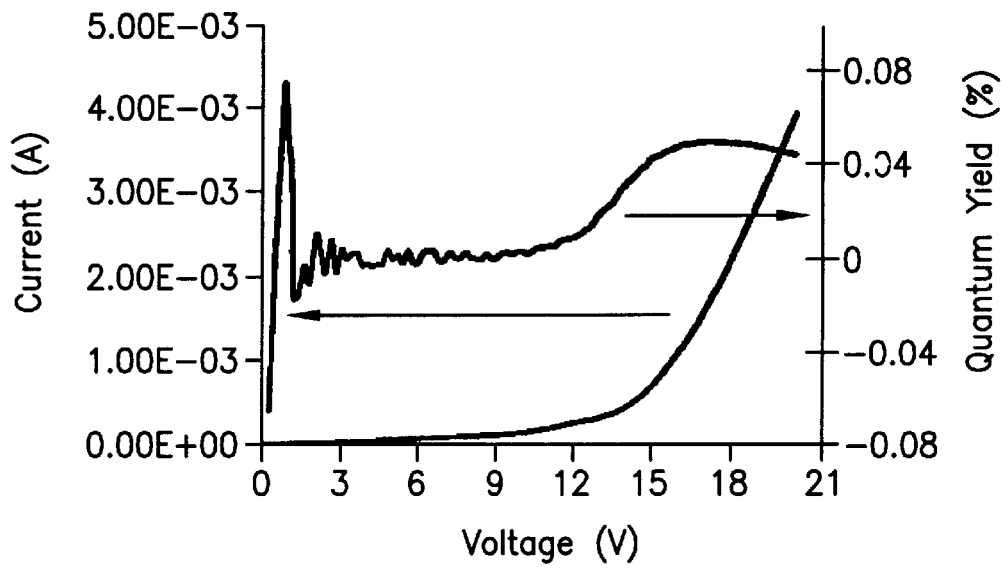
Figure 4:
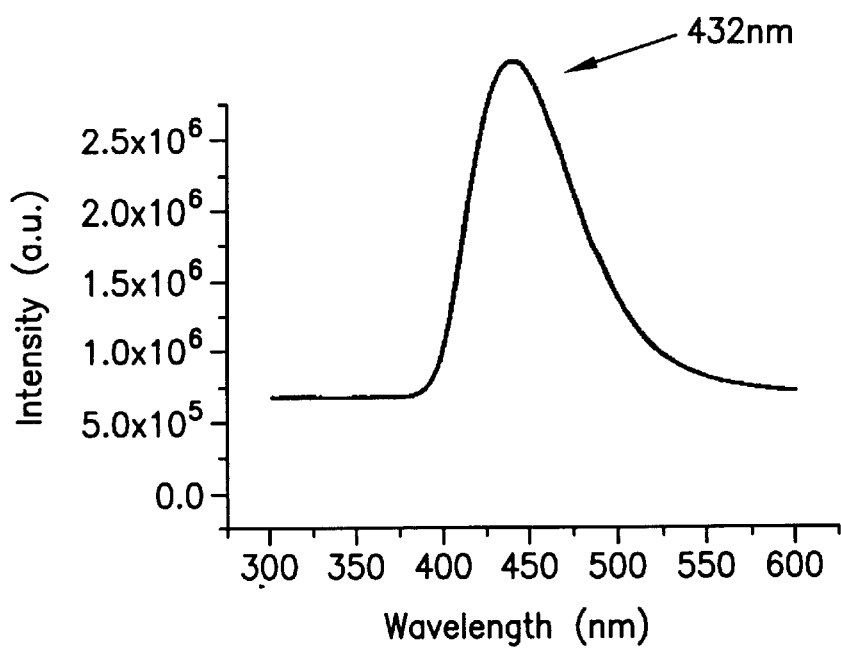

FIG. 4. IV characteristics, Q.E./V and EL spectra of OLED fabricated with a 400 Å COT-H layer.

Figure 5:
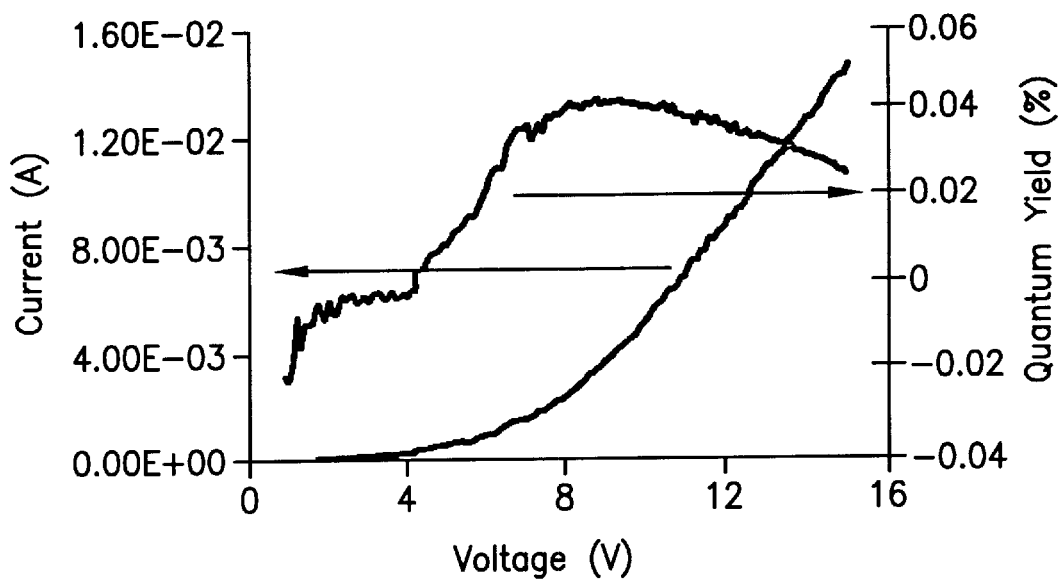
Figure 5:
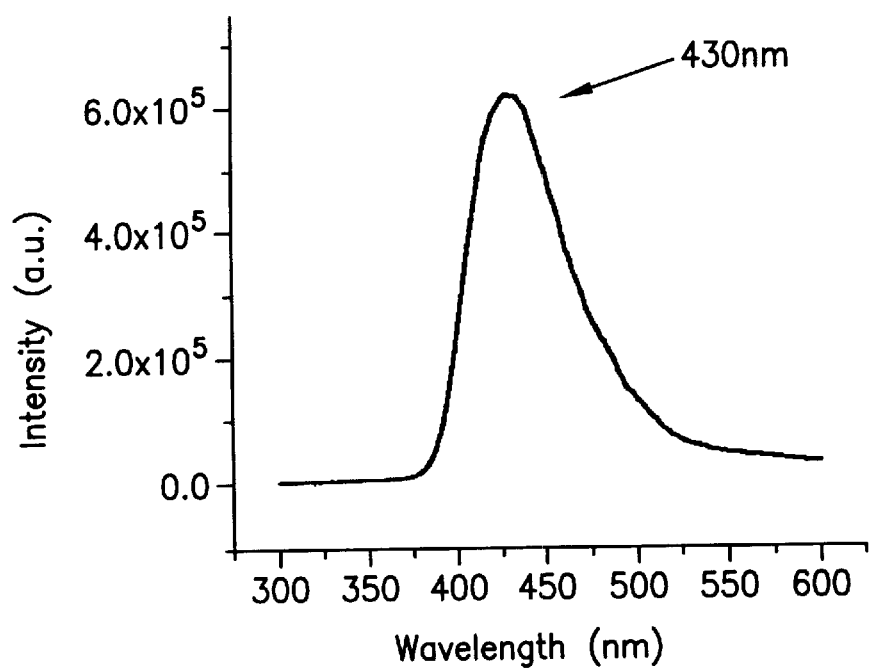

FIG. 5. IV characteristics Q.E./V and EL spectra of OLED fabricated with a 200 Å COT-Me layer.

Figure 6:
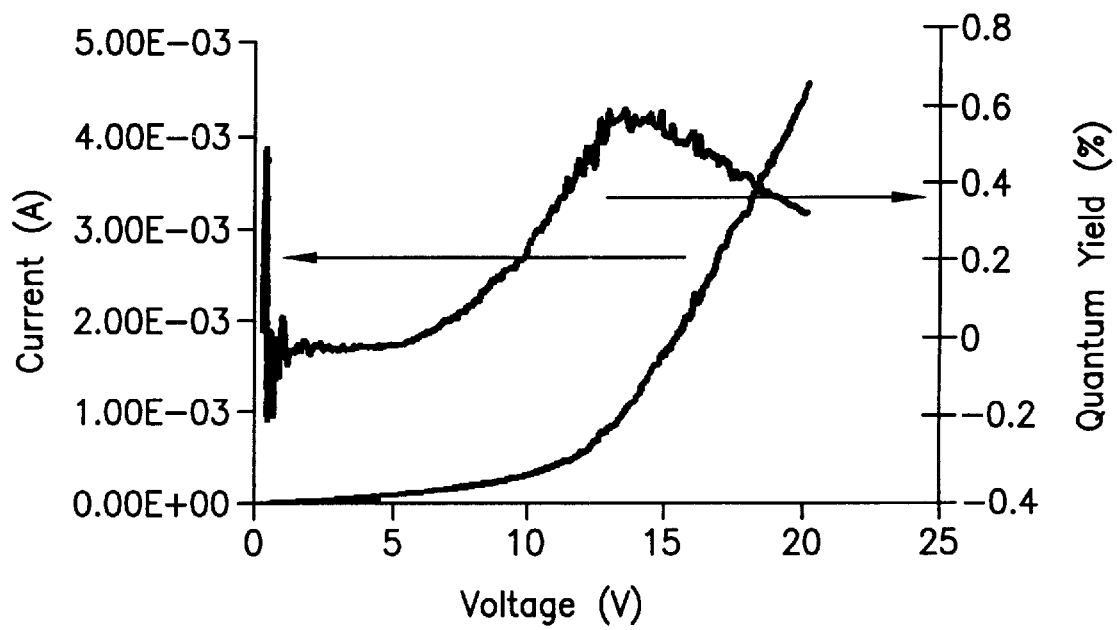
Figure 6:
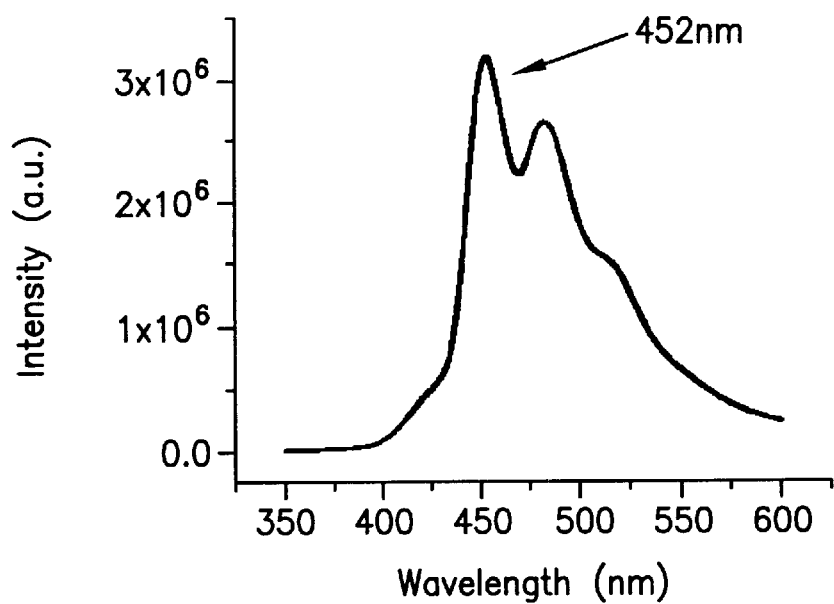

FIG. 6. IV characteristics Q.E./V and EL spectra of OLED fabricated with 1% perylene doped into the NPD layer followed by a 400 Å COT-Me layer.

Figure 7:
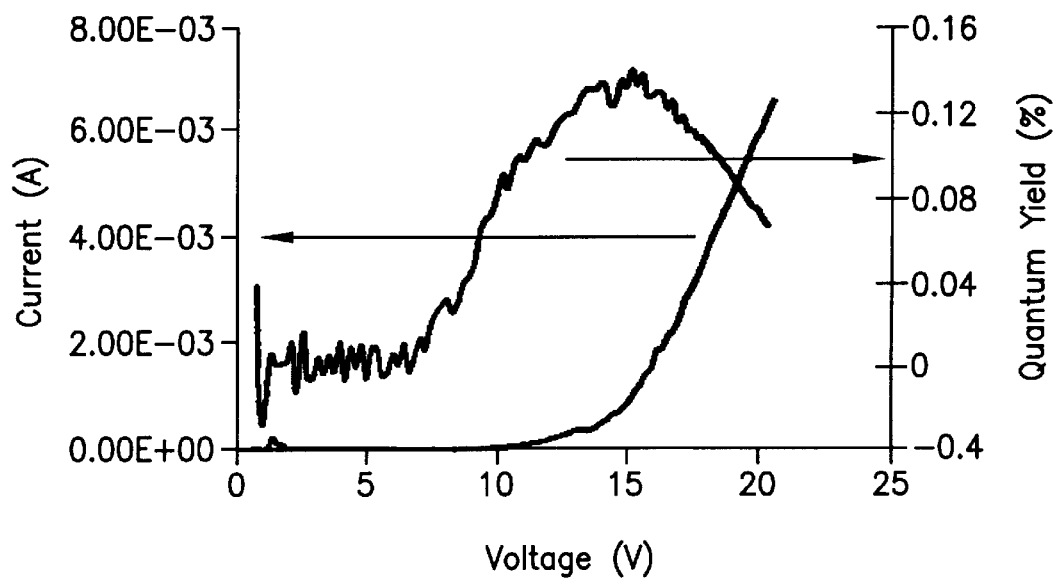
Figure 7:
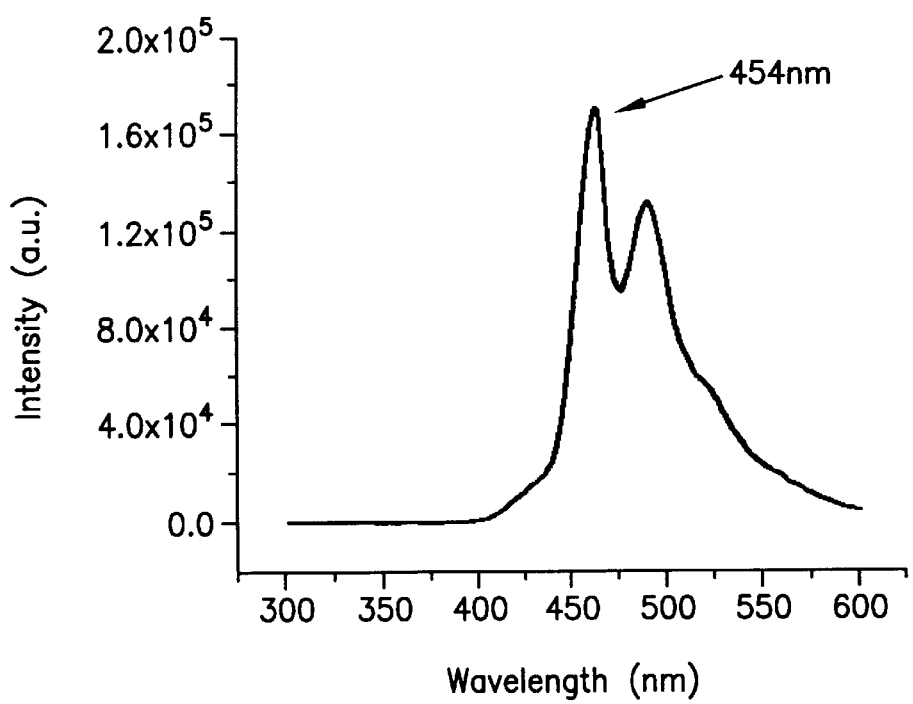

FIG. 7. IV characteristics Q.E./V and EL spectra of OLED fabricated with 1% perylene doped into the NPD layer followed by a 400 Å COT-H layer.

Figure 8:
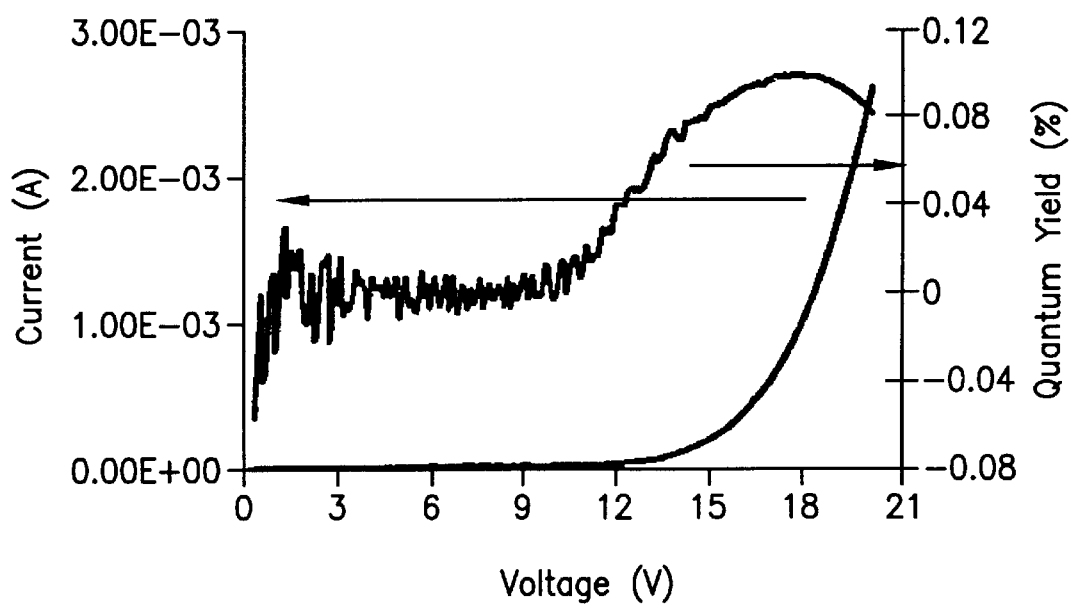
Figure 8:
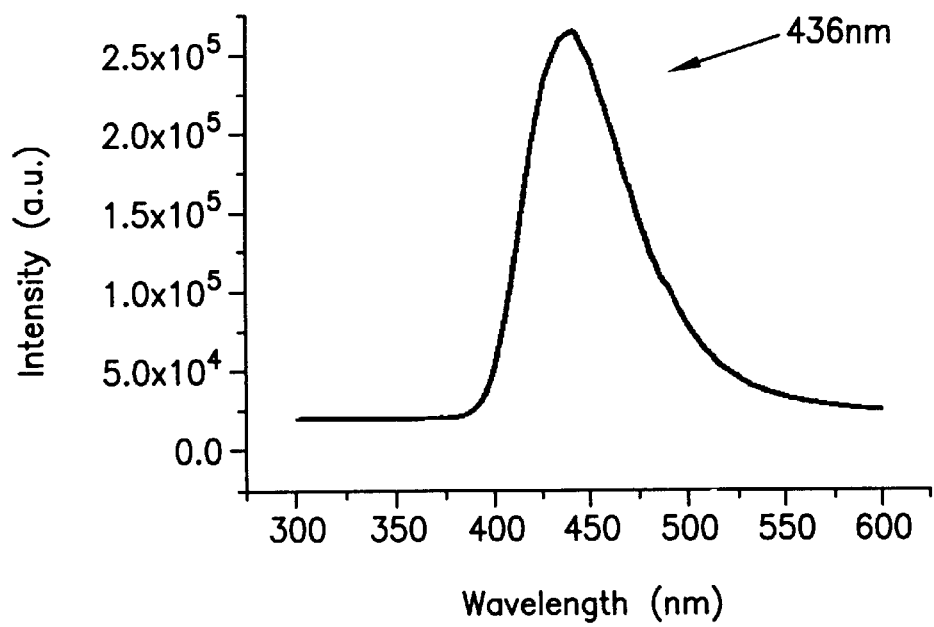

FIG. 8. IV characteristics Q.E./V and EL spectra of OLED with a 400 Å NPD layer and with 1% perylene doped into the NPD layer followed by a 400 Å COT-H layer.

Figure 9:
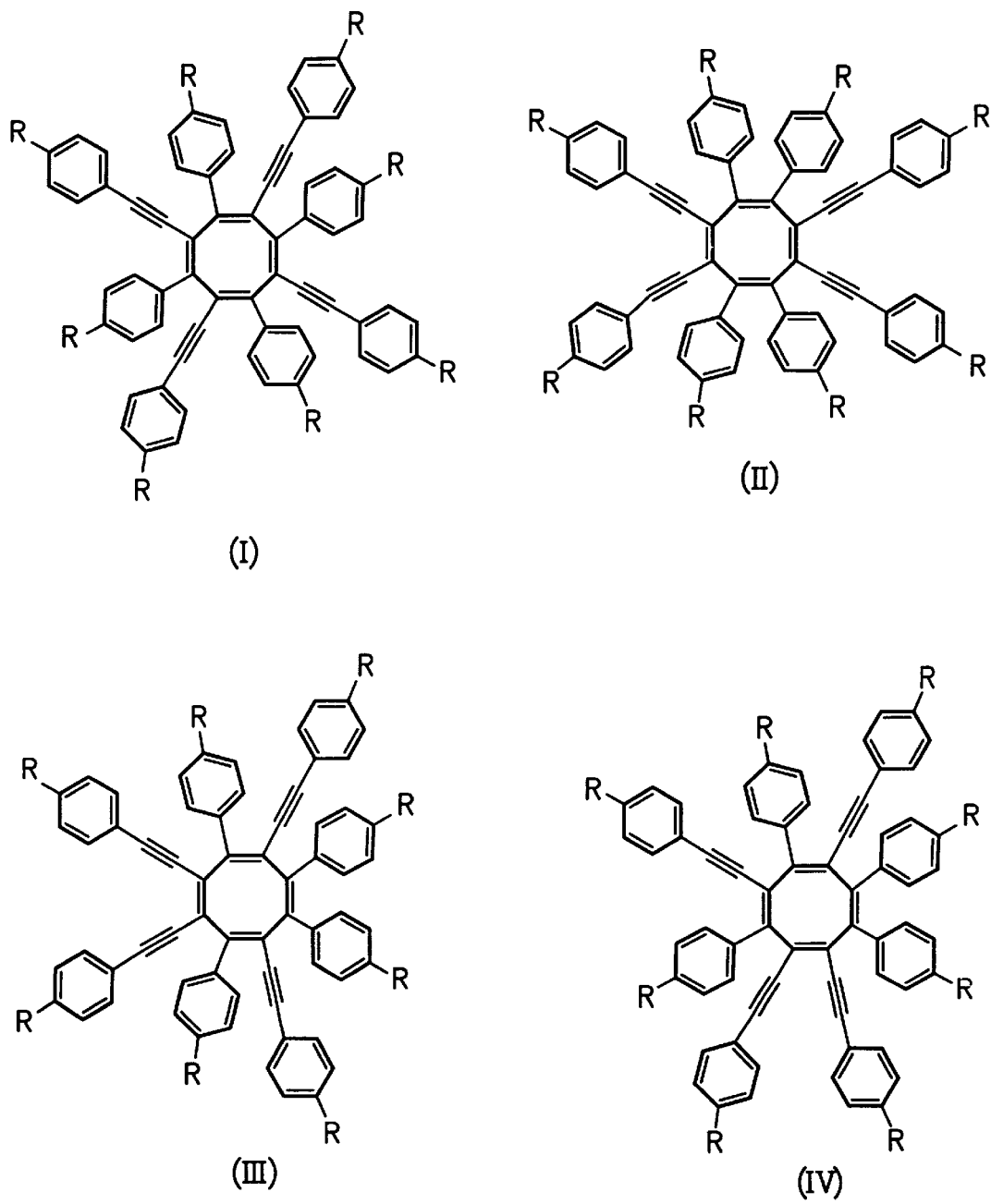

FIG. 9. General depiction of four possible isomeric cyclooctatetraenes which can be formed from the starting butadiyne if the ligands and other carbons of the starting butadiyne maintain their initial connectivity with no structural rearrangement. Isomer IV has neither a mirror plane nor a center of symmetry. NMR arguments suggest that the ruthenium catalyzed reaction discussed herein can yield isomer IV.

Figure 10:
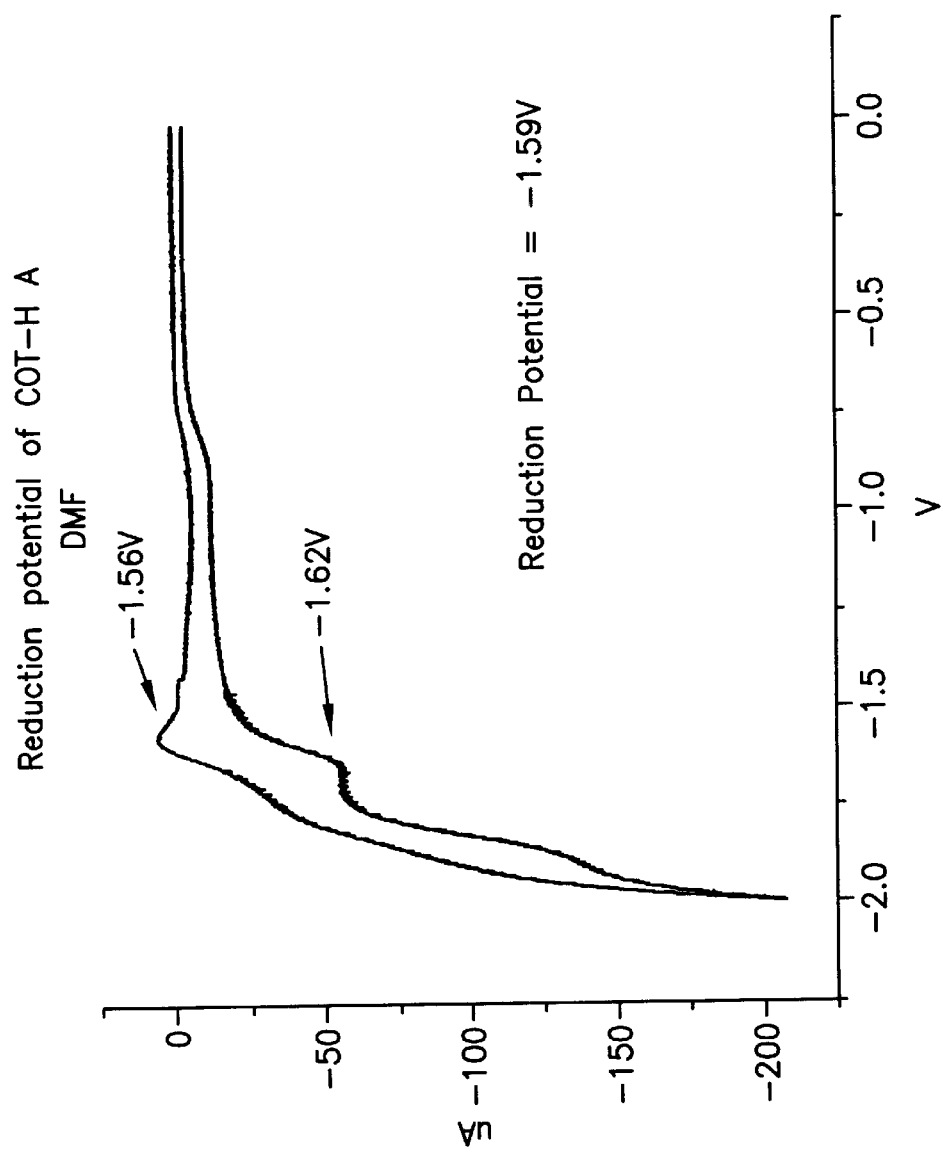

FIG. 10. Cyclic voltammetry on COT-H. (Reduction potential=−1.59 V v. SCE).

Figure 11:
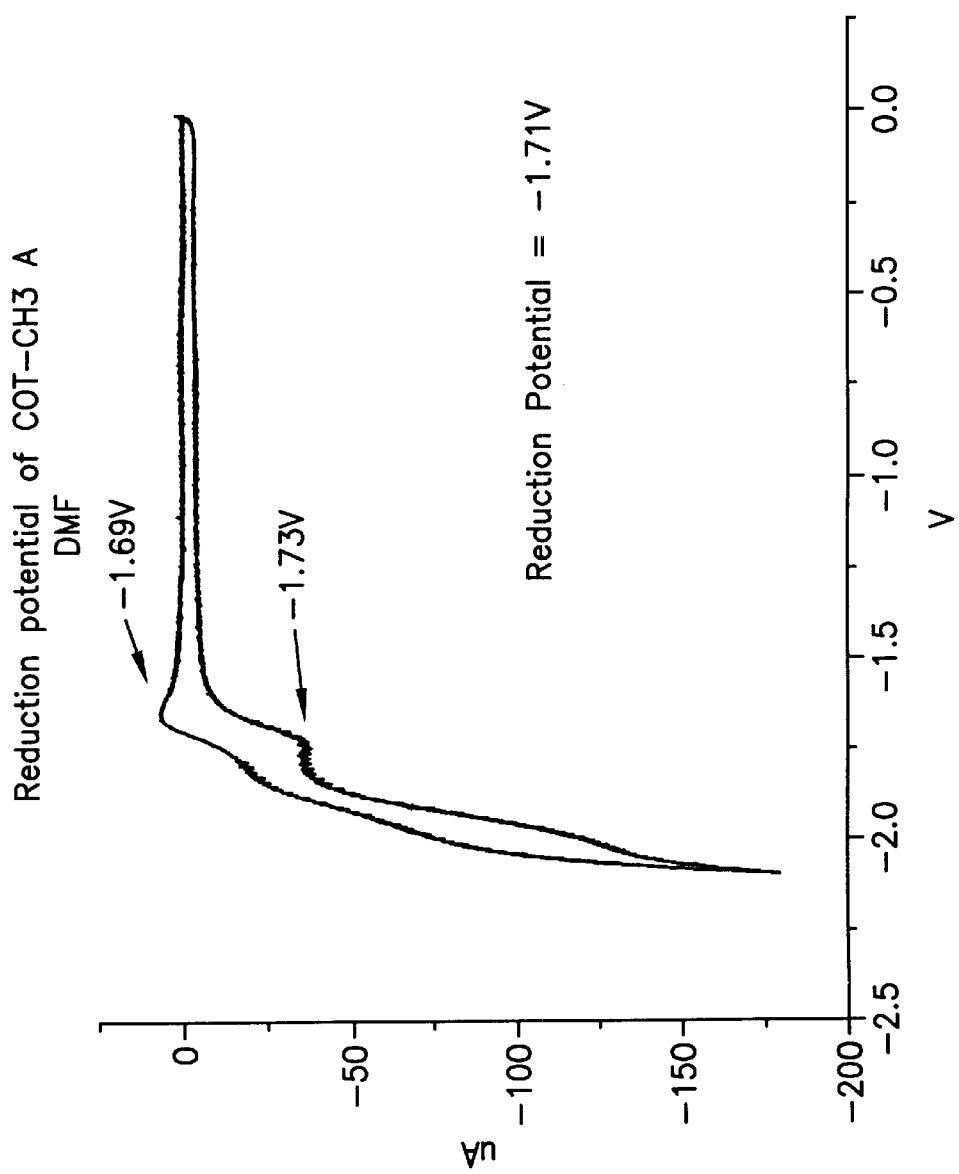

FIG. 11. Cyclic voltammetry on COT-CH3. (Reduction potential=−1.71 V v. SCE).

Figure 12:
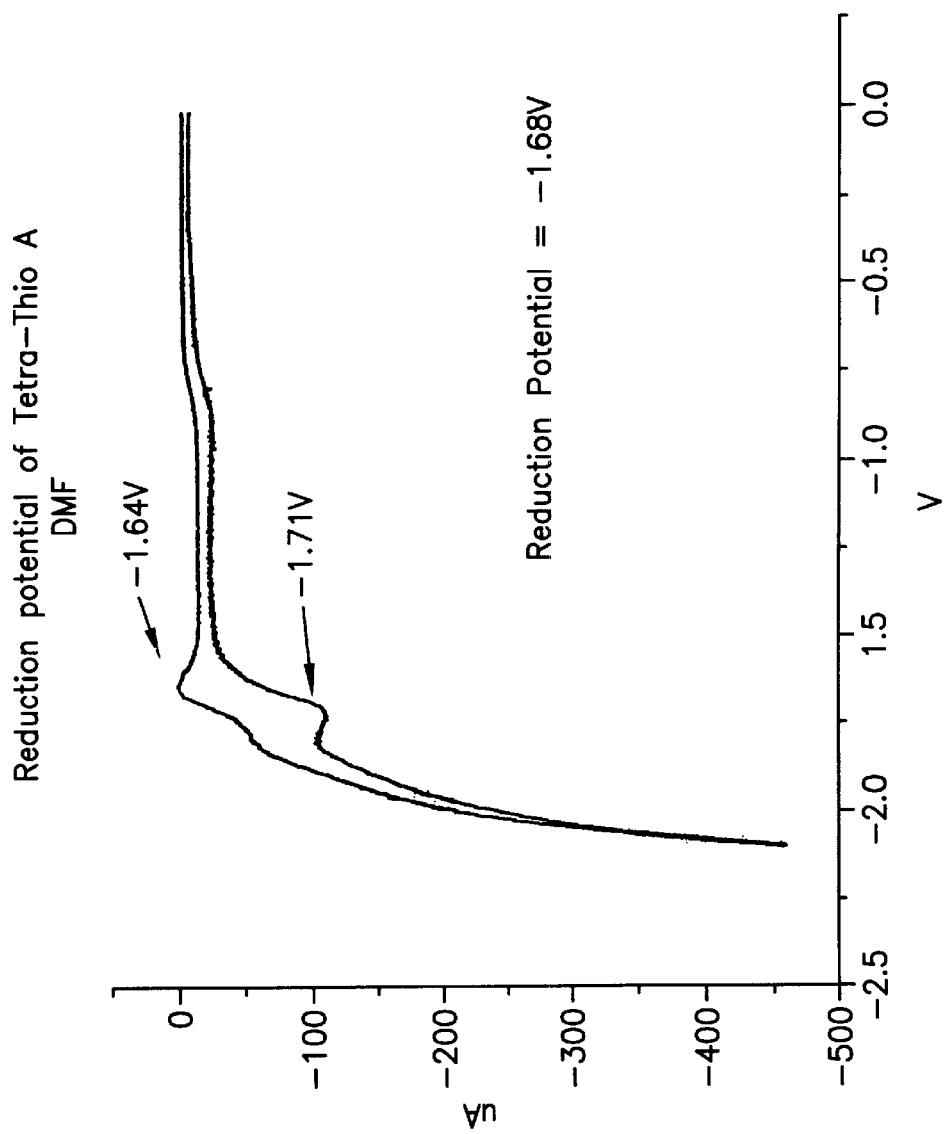

FIG. 12. Cyclic voltammetry on tetra thienyl derivative (COT-S). (Reduction potential=−1.68 V v. SCE)

Figure 13:
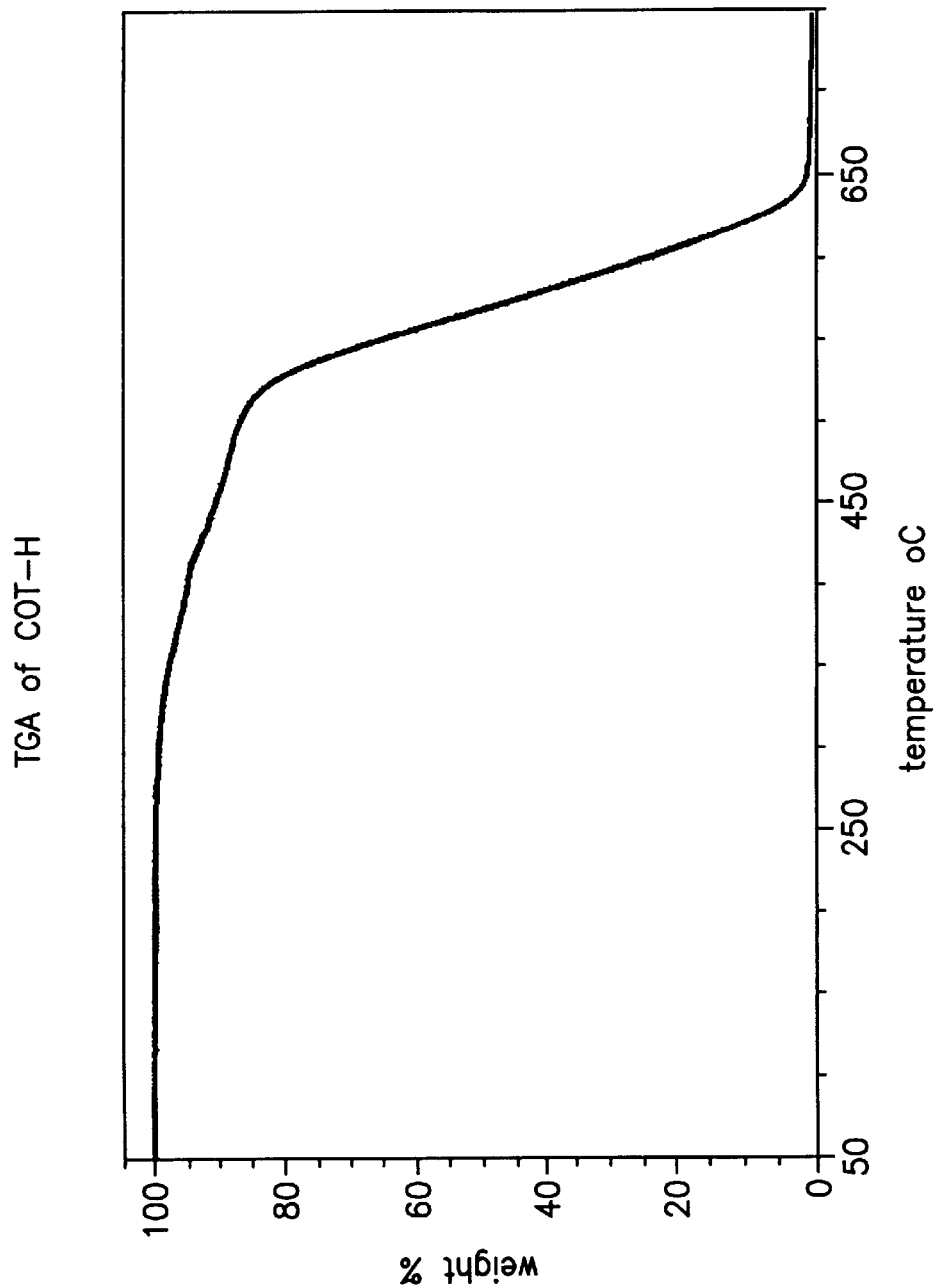

FIG. 13. Thermogravimetric analysis ("TGA") of COT-H.

Figure 14:
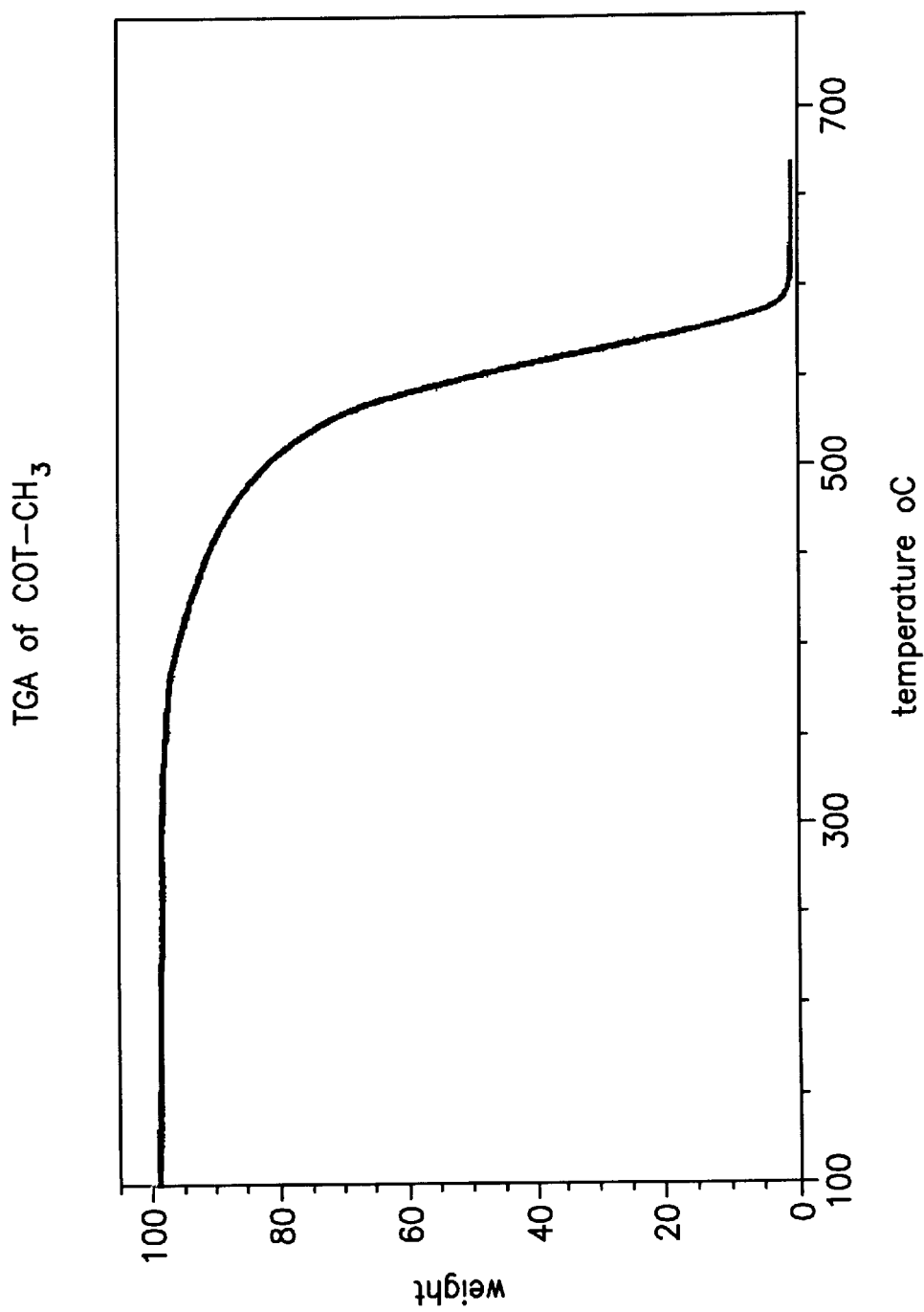

FIG. 14. Thermogravimetric analysis ("TGA") of COT-CH3.

Figure 15:
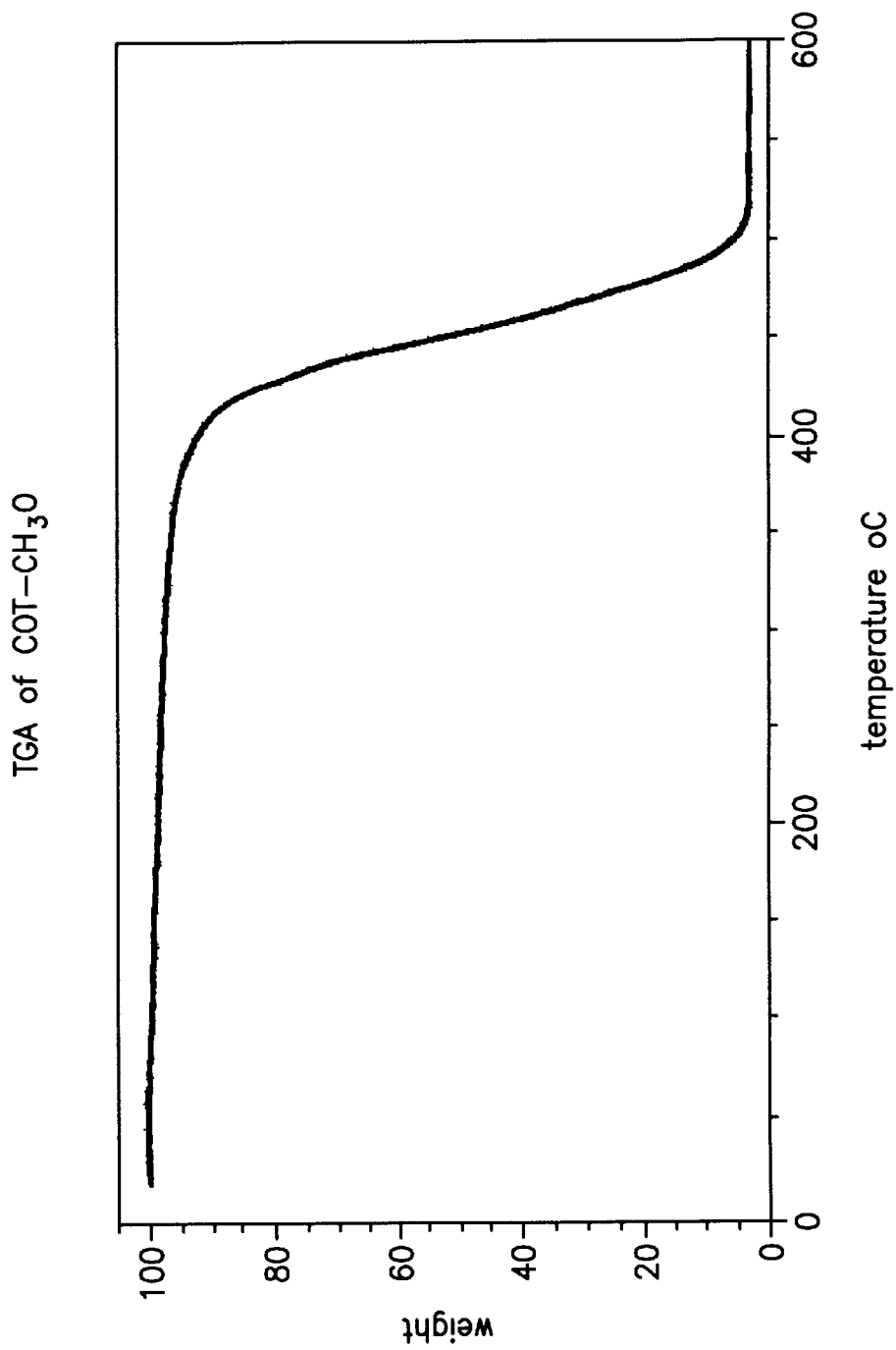

FIG. 15. Thermogravimetric analysis ("TGA") of COT-CH3O

Figure 16:
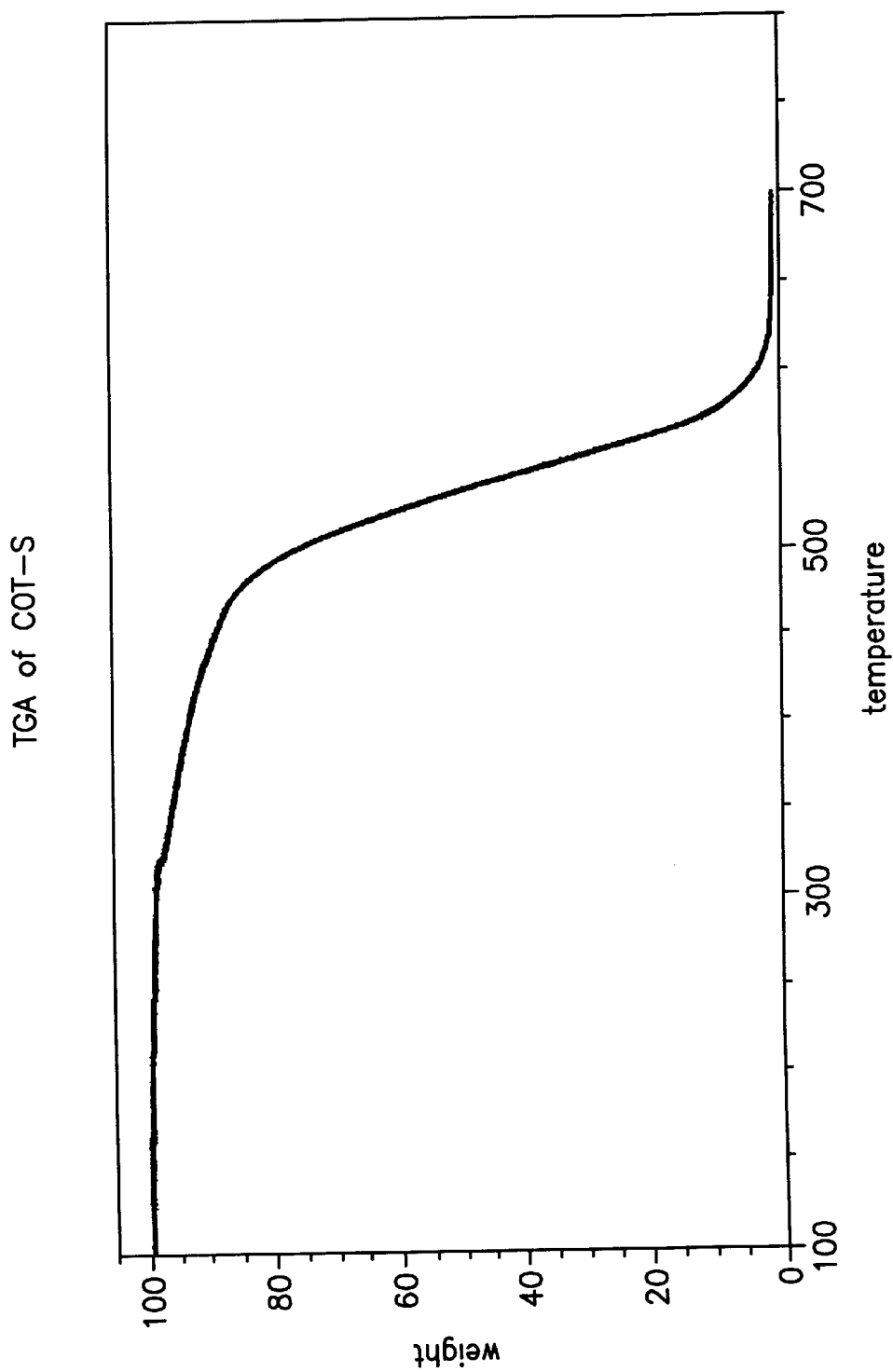

FIG. 16. Thermogravimetric analysis ("TGA") of COT-S.

Figure 17:
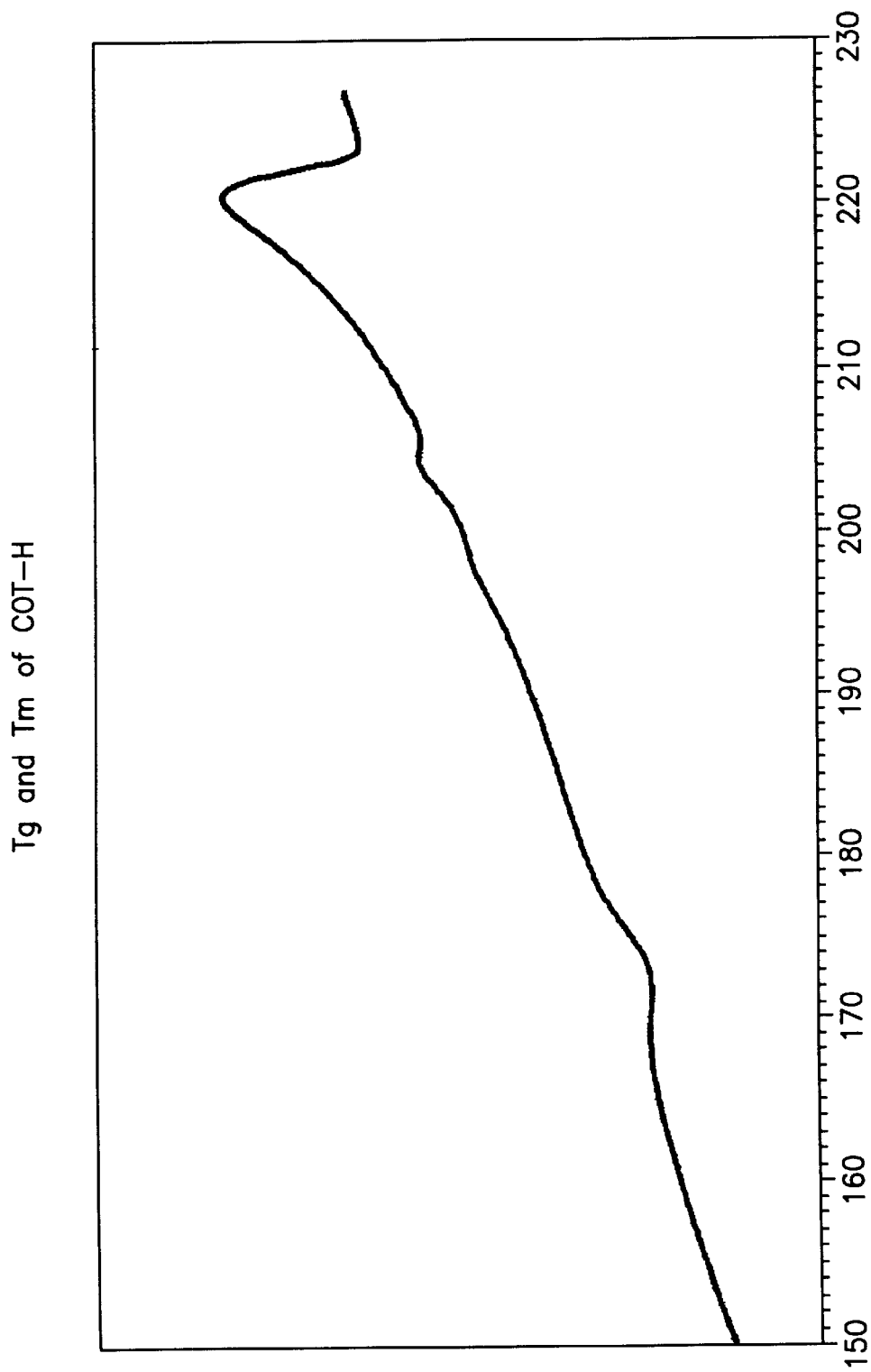

FIG. 17. Differential scanning calorimetry ("DSC") of COT-H giving glass transition (Tg) and melting point (Tm)

Figure 18:
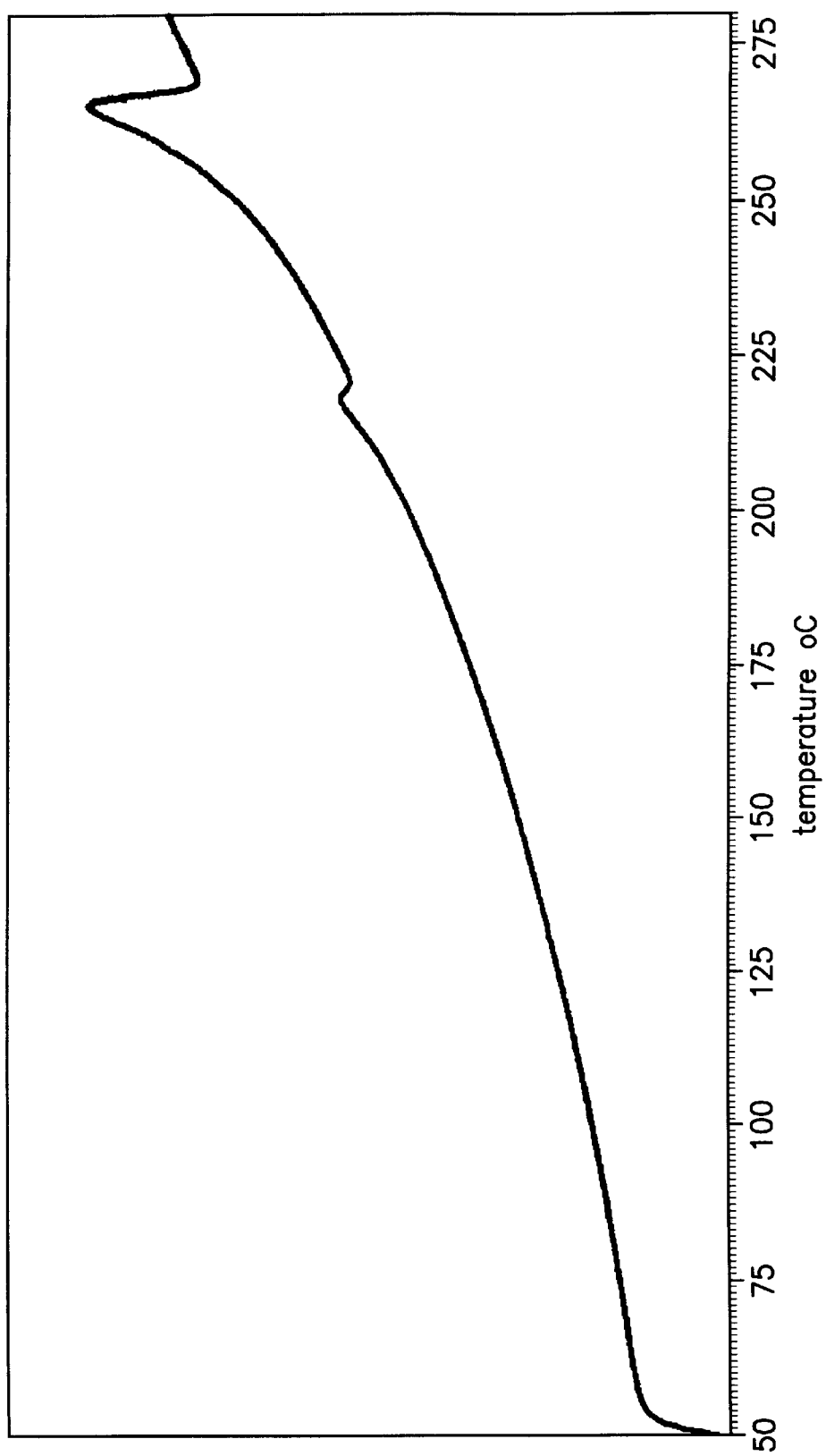

FIG. 18. Differential scanning calorimetry ("DSC") of COT-CH3 giving glass transition (Tg) and melting point (Tm)

Figure 19:
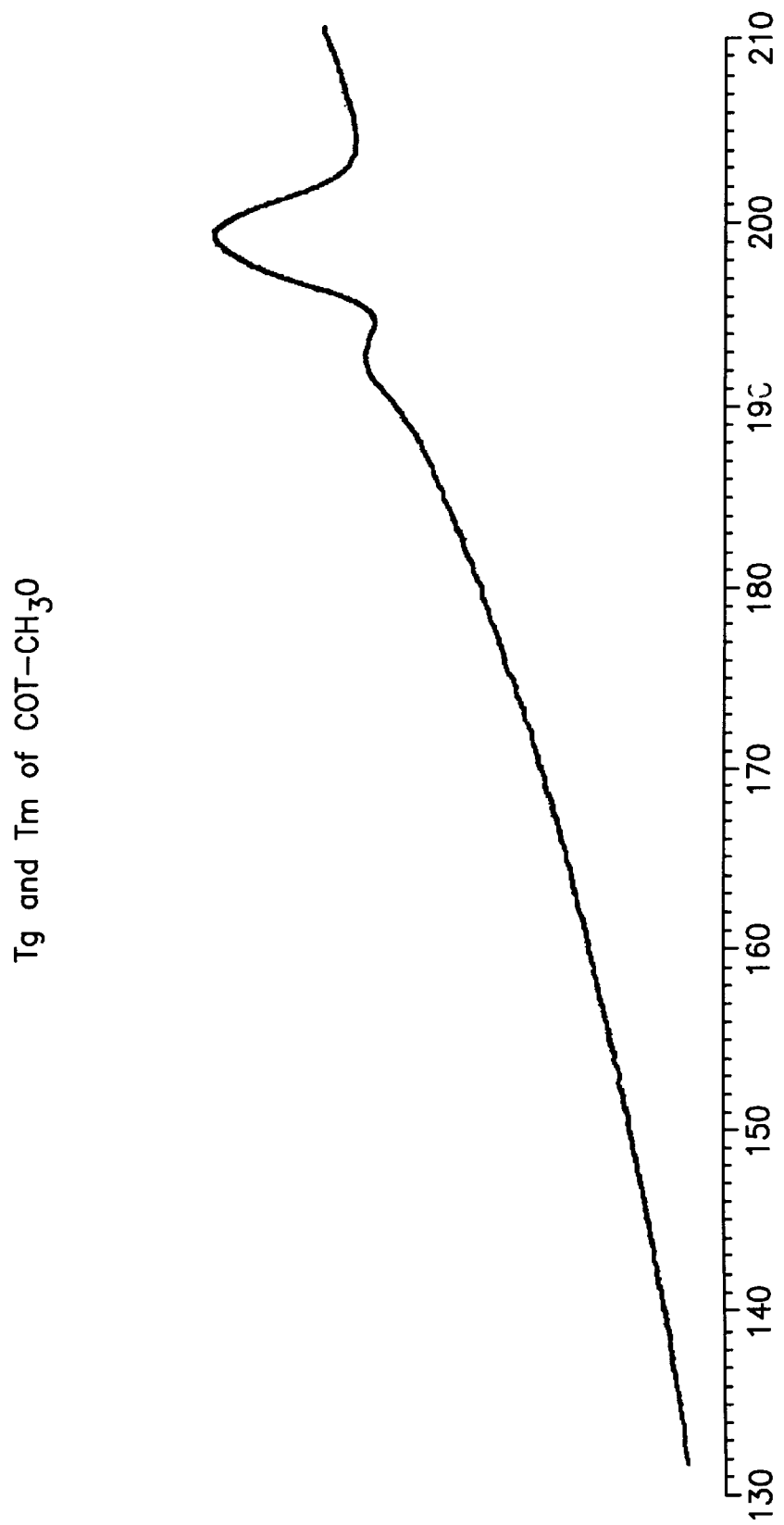

FIG. 19. Differential scanning calorimetry ("DSC") of COT-CH3O giving glass transition (Tg) and melting point (Tm)

V. DETAILED DESCRIPTION OF THE INVENTION

The present invention is directed to the synthesis of certain cyclooctatetraene derivatives and to organic light emitting devices (OLEDs) comprising electron transporting layers (ETLs) comprising derivatives of cyclooctatetraene. These devices include OLEDs wherein the hole transporting layer (HTL) comprises the emissive molecules and these include OLEDs wherein there is a separate emissive layer.

The synthesis can be used to prepare any cyclooctatetraene (COT) derivative. The most general form is shown below and would be made from four different acetylenes. The synthesis would couple these four acetylenes randomly into COT derivatives.

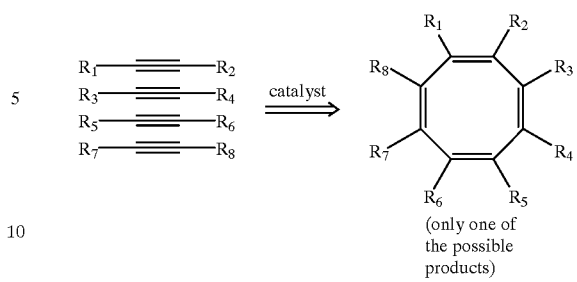
(only one of the possible products)

A preferred embodiment is the coupling of either a symmetric acetylene or diacetylene. When coupling the diacetylene an asymmetric derivative is obtained, since only one of the acetylenic groups is involved in the cyclotetramerization.

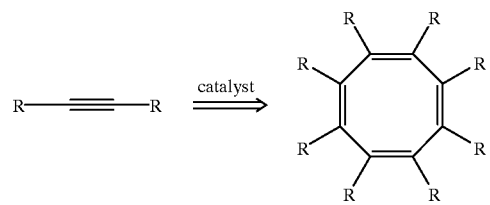

The invention is further directed to a cyclooctatetraene molecule of the formula

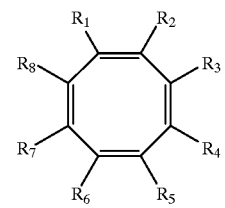

wherein $R_1$ through $R_8$ are selected from the group consisting of alkyl, aryl and alkynyl and wherein at least one member of $R_1$ through $R_8$ is different from the other members of $R_1$ through $R_8$. As an example, $R_1$ could be phenyl and $R_2$ through $R_8$ could be tolyl. Such a product could be obtained by use of two distinct alkyne monomers using the chemistry described below. The invention includes embodiments using more than one alkyne monomer.

The invention is also directed to the above-noted cyclooctatetraene molecule wherein $R_1$ through $R_8$ are selected such that only four members of the set $R_1$ through $R_8$ are identical, with the proviso that no three adjacent members of the set $R_1$ through $R_8$ are identical. The invention is also directed to the above-noted cyclooctatetraene molecule wherein $R_1$ through $R_8$ are selected such that there is a first group of four members of the set $R_1$ through $R_8$ that are identical and there is a second group consisting of the remaining four members of the set $R_1$ through $R_8$ that are identical, with the proviso that the members of the first group are different from the members of the second group and that no three adjacent members of the set $R_1$ through $R_8$ are identical. An example would be $R_1$, $R_3$, $R_5$, and $R_7$ equal to phenyl and $R_2$, $R_4$, $R_6$, and $R_8$ equal to tolyl. This embodiment would not allow $R_1$, $R_2$, and $R_3$ (adjacent members) to each be phenyl.

The substituents $R_1$ through $R_8$ may be derived from arene molecules. By the term "derived from" we mean that as in a naphthyl substituent is derived from a naphthalene molecule. The substituents may be phenyl, tolyl, naphthyl, thienyl and benzthienyl. The substituents $R_1$ through $R_8$ may be derived from aromatic hydrocarbons substituted with an electron withdrawing group or groups as exemplefied by, but not limited by, CN, halogen, nitro, carbonyl and imine. The substitutuents $R_1$ through $R_8$ may be derived from heteroaromatic quinolines and pyridines. The substituents may be of different geometrical isomers as those in COT derivatives arising from di-p-tolylbutadiyne, di-o-tolylbutadiyne, and di-m-tolylbutadiyne.

In an embodiment using a single alkyne monomer, one could have four members of the set $R_1$ to $R_8$ identical (such as four members equal to phenyl), with the other four members of the set $R_1$ to $R_8$ identical (such as four member equal to tolyl), with the proviso that no three adjacent members of $R_1$ to $R_8$ are identical. To define the term "adjacent to" with reference to the above figure, $R_3$ is adjacent to $R_2$ and $R_4$, and similarly for the other members of $R_1$ to $R_8$. "Adjacent to" means "nearest to" in the sense that $R_3$ is nearest to $R_2$ and $R_4$ in the planar representation of the molecule.

As to terminology, terms such as "aromatic hydrocarbon", "arene", and "organometallic" are given the meaning of the skilled artisan. Of the last, "organometallic" is as generally understood by one of ordinary skill, as given, for example, in "Inorganic Chemistry" (2nd edition) by Gary L. Miessler and Donald A. Tarr, Prentice-Hall (1998). Discussions of the appearance of color, including descriptions of CIE charts, may be found in Color Chemistry, VCH Publishers, 1991 and H. J. A. Dartnall, J. K. Bowmaker, and J. D. Mollon, Proc. Roy. Soc. B (London), 1983, 220, 115–130.

The present invention will now be described in detail for specific preferred embodiments of the invention, it being understood that these embodiments are intended only as illustrative examples and the invention is not to be limited thereto.

V.A. Overview of Synthetic Work

Dihydridocarbonyltris (triphenylphosphine) ruthenium which has been activated by treatment with a stoichiometric amount of styrene catalyzes the cyclotetramerization of diphenylbutadiyne to give the unsymmetrical 1,2,4,6-tetraphenyl-3,5,7,8-tetrakis (phenylethynyl) cyclooctatetraene in high yield. When irradiated at 310–320 nm, solutions of this material fluoresce at 392 nm with a quantum yield of 16%. Solutions of the corresponding cyclooctatetraene derivative prepared from di-p-tolyl-butadiyne and di-p-methoxyphenylbutadiyne fluoresce at 402 nm and 412 nm with quantum yields of 47% and 79% respectively.

V.A.1. Background

Diphenylbutadiyne undergoes tetramerization on treatment with dihydrido carbonyl tris(triphenylphosphine) ruthenium, which has been activated by treatment with a stoichiometric amount of styrene. (H. Guo, G. Wang, M. A. Tapsak, W. P. Weber, Macromolecules, 1995, 28, 5686). Similar successful cyclotetramerization of di-p-tolylbutadiyne and di-p-methoxyphenylbutadiyne have been carried out.

This reaction is extremely efficient and selective. The tetramer of diphenylbutadiyne is formed in 86% yield after purification by chromatography and recrystallization. The molecular weight of the tetramer has been established by mass spectrometry. The major fragmentation pathway of the parent cation radical ("molecular ion") is loss of diphenylbutadiyne to give a trimer cation radical. The tetramer is quite thermally stable. It does not undergo loss of weight in thermogravimetric analysis ("TGA") until over 310° C. Above this temperature it undergoes steady weight loss so that by 650° C., only 2% of the initial sample weight remains. This is important because the result shows that the COT does not thermally polymerize.

Transition metal catalyzed cyclotrimerization of acetylenes to yield benzene derivatives is well known. (M. Berthelot, Ann., 1866, 139, 273). On the other hand, the transition metal catalyzed cyclotetramerization of acetylenes to yield cyclooctatetraene derivatives is much less common. Reppe first reported that acetylene itself could be tetramerized by nickel catalysts to yield cyclooctatetraene. (W. Reppe and W. J. Schweckendiek, Ann., 1948, 560, 104; G. Schröder, Cyclooctatetraenes, Veriag-Chemie: Weinheim, Germany, 1965).

V.A.2. Possible isomers

Assuming that the phenyl groups, and the other carbon atoms of the starting material diphenylbutadiyne maintain their initial connectivity with no structural rearrangement, there are four possible isomeric cyclooctatetraene products. These products are illustrated in FIG. 9 and they are named as follows:

1,3,5,7-tetraphenyl-2,4,6,8-tetrakis(phenylethynyl) cyclooctatetraene (I)

1,2,5,6-tetraphenyl-3,4,7,8-tetrakis(phenylethynyl) cyclooctatetraene (II)

1,2,4,7-tetraphenyl-3,5,6,8-tetrakis(phenylethynyl) cyclooctatetraene (III)

1,2,4,7-tetraphenyl-3,5,7,8-tetrakis(phenylethynyl) cyclooctatetraene (IV)

In terms of symmetry, I has a mirror plane and a center of symmetry, whereas II and III only have mirror planes. The final isomer IV has neither a mirror plane nor a center of symmetry.

V.A.3. Evidence of unsymmetric isomer

The structure of the tetramer actually obtained has been determined based upon spectroscopic evidence. The data indicate that the ruthenium catalyzed cyclotetramerization of diphenylbutadiyne yields a single isomeric product—the unsymmetrical cyclooctatetraene IV.

Specifically, the spectra of the cyclotetramers formed from diphenylbutadiyne, di-p-tolylbutadiyne and di-p-methoxyphenylbutadiyne are consistent with the unsymmetrical isomer IV. Specifically, the 1H NMR of the cyclotetramer formed from di-p-tolylbutadiyne has seven resonances for the methyl groups. Six of these are of equal intensity while one has an intensity which is twice as large. Similarly, the 13C NMR of the cyclotetramer formed from di-p-methoxyphenyl butadiyne shows seven resonances due to non-equivalent methoxy groups. The intensity of one of these is twice that of the other signals. Apparently, two of the methyl groups and two of the methoxy groups fortuitously have identical chemical shifts This is consistent with the unsymmetrical tetramer IV. In contrast, isomers I and II would be expected to show two signals due to the methyl groups, while isomer III would be expected to show four resonances due to the methyl groups. Eight distinct resonances for the acetylenic carbons are observed in the 13C NMR for the tetramer formed from diphenylbutadiyne. Likewise, eight resonances due Lu acetylenic carbons are seen in the 13C NMR of both di-p-tolylbutadiyne and di-p-methoxyphenylbutadiyne. An analysis similar to that above predicts eight acetylenic resonances for isomer IV, two each for isomer I or II and four for isomer III.

Nevertheless, this analysis is based on an assumption that cyclooctatetraenes are planar. In fact, cyclooctatetraenes are not planar. Rather, they are tub shaped molecules that undergo both ring inversion and double bond shift processes, as shown by variable temperature 1H NMR.

For example, in the case of cyclooctatetraenyl-2,3,4,5,6, 7-d6-dimethylcarbinol, the methyl groups are non-equivalent at low temperature. At higher temperature, they broaden and coalesce at −2° C., and finally become a sharp single line at higher temperature. A doublet is also observed for the ring proton; however, the temperature at which this doublet coalesces is higher: +41° C. The activation energy of these two processes is 14.7 kcal/mol and 17.1 kcal/mol respectively. (F. A. L. Anet, A. J. R. Bourn, and Y. S. Lin, J. Am. Chem. Soc., 1964, 86, 3576).

To address the issue of the non-planarity of cyclooctatetraenes, we carried out variable temperature 1H NMR on samples of the tetramer of di-p-tolylbutadiyne. Our results eliminate the possibility that the eight methyl signals were due to the non-planar structure expected for cyclooctatetraenes. Specifically, on heating the sample from room temperature to 100° C., no change was observed either in the number of resonances due to the methyl groups nor in their peak shapes. Neither broadening nor coalescence was detected. On this basis, we believe that our cyclooctatetraenes are undergoing rapid double bond shift processes. Under these conditions, predictions derived from a planar representation of cyclooctatetraene will be correct.

Interestingly, cyclotrimerization and cyclotetramerization of methyl propiolate by a tetrakis(phosphorous trihalide) nickel(0) complex gave 1,2,4-tricarbomethoxybenzene and the unsymmetrical 1,2,4,6-tetracabethoxycyclooctatetraene as the sole products. (J. R. Leto and M. F. Leto, J. Am. Chem. Soc., 1961, 83, 2944) The reason for the regioselectivity observed which favor the formation of the unsymmetrical cyclooctatetraene is not understood.

The catalyst dihydridocarbonyltri(triphenylphosphine) ruthenium has been activated by treatment with a stoichiometric amount of styrene at 135° C. This serves to remove hydrogen from the ruthenium complex and yields ethylbenzene and a site of coordinate unsaturation. (H. Guo, G. Wang, M. A. Tapsak, W. P. Weber, Macromolecules, 1995, 28, 5686)

V.A.4. Experimental details

V. A.4. a. Spectroscopy $^1$H and $^{13}$C NMR spectra were obtained on a Bruker 500 spectrometer operating in the Fourier transform mode. Five percent w/v chloroform-d solutions were used to obtain $^1$H NMR and $^{13}$C NMR spectra. Residual chloroform was used as an internal standard. Predictions of $^1$H NMR chemical shifts were generated by using ACD/HNMR-2.5 software from Advanced Chemistry Development, Inc., Toronto, Canada. $^{13}$C NMR spectra were run with both broad band proton decoupling and with off resonance proton decoupling. The multiplicity observed in the off resonance $^{13}$C NMR spectra permits the determination of the number of protons bonded to each particular carbon (H. Günther,. NMR Spectroscopy 2nd Edition, J. Wiley & Sons, Chichester, England, 1995. 269–270). IR spectra of neat films on NaCl plates were recorded on a Perkin-Elmer Spectrum 2000 FT-IR spectrometer. UV spectra of methylene chloride solutions were acquired on a Shimadzu UV-260 ultraviolet visible spectrometer. Fluorescence spectra were performed on a PTI instrument, equipped with a model A1010 Xe/Hg lamp and a model 710 photomultiplier diffraction detector. Spectra were obtained on methylene chloride solutions which had been degassed by bubbling argon through them for 10 min. Fluorescence quantum yield were determined relative to that of N-methyl carbazole.

V.A.4.b.Thermal Properties:

The glass transition temperature $T_g$ and the melting point $T_m$ of the tetramers were determined on a Perkin-Elmer DSC-7 instrument. The melting point of indiurn (156 ° C.) was used to calibrate the DSC. The analysis program was 10° C./min from 50 to 300° C. TGA of the tetramers were measured on a Shimadzu TGA-50 instrument. The temperature was increased by 5° C./min from 25 to 700° C.

V.A.4.c. Mass spectrometry

High-resolution mass spectra were run at the University of California Riverside Mass Spectrometry Facility on a VG-ZAB instrument. Exact masses were determined by peak matching against known peaks of polypropylene glycol (795.5447 and 853.5865). V.A.4.d. Reagents:

Cuprous chloride, cuprous iodide, 2,7-dimethyl-3,5-octadiyne-2,7-diol, diphenylbutadiyne, p-bromoanisole, phenylacetylene, p-tolylacetylene, trimethylsilylacetylene, and bis(triphenylphosphine)palladium dichloride, tetrakis (triphenylphosphine)palladium, were purchased from Aldrich. Dihydridocarbonyltris(triphenylphosphine)ruthenium catalyst (J. I. Levison.; S. D. Robinson, J Chem. Soc., A, 1970, 2947.) was prepared from rutheniuim trichloride hydrate (Aldrich).

V.A.4.e. Preparation of intermediates

Preparation of Di-p-tolylbutadiyne

In a 100 mL round bottom flask equipped with a gas inlet tube, was placed a Teflon covered magnetic stirring bar, p-tolylacetylene (5.0 g, 43 mmol), methanol 5 mL, pyridine 1.25 mL, and CuCl (0.2 g, 2 mmol). The reaction mixture was vigorously stirred while air was bubbled through it (A. Vogel, *Vogel's Textbook of Practical Organic Chemistry*, 4th Ed. Longman, London, England, 1978, p 351) Concentrated HCl (2 mL) and saturated sodium chloride (10 mL) was added. The precipitate was isolated by filtration. It was washed with water, dried, and recrystallized from toluene to give 3.45 g, 69% yield, mp 181–183° C. (Lit, 183° C. (Kunckell, *Chem. Zentralblatt*, 1913, I,1768)). $^1$H NMR δ: 7.40(d, 4H, J=8.25 Hz), 7.12(d, 4K J=8.25 Hz), 2.35(s, 6H) p-Methoxyphenylethynyl trimethylsilane (K. Takashi.; F. Michiya.; E. Fumihiro.; T. Hisao; Jap. Patent 61 43,149 [86 43149], CA 106:4625 n; K. Takashi; E. Fumihiro; T. Hisao; Jap. Patent 60,217,213 [85,217,213] CA 105: 42449v)

p-Bromoanisole(3.74 g, 20 mmol), tetrakis (triphenylphosphine)palladium (1.16 g, 1 mmol) and CuI (0.381 g, 2 mmol) were placed in a 100 mL three neck round bottom flask, equipped with a pressure equalizing addition funnel and a reflux condenser which was connected to a vacuum line. The third neck of the flask was sealed with a rubber septum. The apparatus was purged with nitrogen three times. Pyridine, (30 mL) was added and the mixture was stirred until it became a single clear phase. Trimethylsilyl-acetylene (1.96 g, 20 mmol) and 20 mL of pyridine were placed in the addition funnel and the solution was added dropwise to the reaction mixture at 45° C. The reaction mixture was heated to 60° C. The progress of the reaction was monitored by TLC (silica gel with hexane/ethyl acetate). When the reaction was complete, it was extracted with ether. The organic solution was dried over anhydrous magnesium sulfate, filtered and the volatile solvents removed by evaporation under reduced pressure. The residue was purified by column chromatography (silica gel with hexane/ethyl acetate). In this way, 2.66g, 65% yield, was obtained. $^1$H NMR δ: 7.39(d, 2H, J=8.75 Hz), 6.80(d, 2H, J=8.75 Hz), 3.78(s, 3H), 0.23(s, 9H).

Di-p-methoxyphenylbutadiyne via Oxidative Coupling of p-Methoxyphenyl acetylene p-Methoxyphenylethynyl trimethylsilane (2.66 g, 13 mmol), and a solution of KOH (1.2 g, 21 mmol) in 20 mL of methanol were placed in a 50 mL round bottom flask equipped with a Teflon covered magnetic stirring bar. The reaction was stirred at 50° C. for 2 h. The progress of the reaction was monitored by TLC as above. When the reaction was complete, it was extracted with ether, washed with water three times, dried over anhydrous magnesium sulfate, filtered and the volatile solvents removed by evaporation under reduced pressure. The oily product, p-methoxyphenyl acetylene (1.54 g, 12 mmol) was placed in a 50 mL round bottom flask as above. Methanol (5 mL), pyridine (1.25 mL) and CuCl (0.2 g, 2 mmol) were added. Air was bubbled through the reaction mixture for 2 h. The coupling reaction was monitored by TLC. When the reaction was complete, it was extracted with ether. The ether solution was washed with water, dried over anhydrous magnesium sulfate, filtered and the solvents removed by evaporation under reduced pressure. The residue was recrystallized from methanol to give 0.92 g, 35%, yield, mp 138° C. (Lit., 144 ° C. (M. Cariou, *Tetrahedron*, 1991, 47(4/5), 799))$^1$H NMR δ: 7.44 (d, 4H, J=8.5 Hz), 6.83(d, 4H, J=8.5 Hz), 3.80(s, 6H).

Di-p-methoxyphenylbutadiyne

Bis(triphenylphosphine)palladium dichloride (0.7 g, 1 mmol), cuprous iodide (0.02 g, 0.1 mmol) and 0.02 g tetramethylammonium bromide were placed in a three neck flask, equipped with a pressure equalizing additional funnel and a reflux condenser connected to the vacuum line (A. Sarkar; S. Okada; H. Nakanishi, *Helv. Chim. Acta.* 82, 138 (1999)). The apparatus was purged with nitrogen for three times. Nitrogen was bubbled through a solution of p-bromoanisole (3.74 g, 20 mmol), and 2,7-dimethylocta-3,5-diyne-2 7-diol (1.66 g, 10 mmol) in 50 mL dioxane for 10 min. The solution was placed in the addition funnel and was added dropwise to the flask. Nitrogen was bubbled through a solution of NaOH (5.5 g, 0.14 mol) in water (25 mL). This solution was rapidly added. The reaction mixture was refluxed overnight. It was extracted by chloroform and washed by water three times, dried over anhydrous magnesium sulfate, filtered and the volatile was removed under reduce pressure. The residue was purified by column chromatography (silica gel/hexane/methylene chloride) to give 0.75 g of a yellow solid, 29% yield, mp 138° C. $^1$H NMR δ: 7.44(d, 4H, J=8.5 Hz), 6.83(d, 4H, J=8.5 Hz), 3.80(s, 6H).

V.A.5. Working examples of synthesis of derivatives of cyclooctatetraene

V.A.5.a. Synthesis of tetramer of diphenylbutadiyne ("COT-H") Dihydridocarbonyltris(triphenylphosphine)ruthenium(55.1 mg, 60 μmol), toluene 3 mL, and styrene (6.8 μl, 60 μmol) were placed in an Ace pressure tube. The tube and its contents were purged with nitrogen for a few minutes. The tube was sealed and heated at 110° C. until the color of the catalyst solution had changed to orange. This color change indicates that the catalyst has been activated (H. Guo.; G. Wang; M. A. Tapsak; W. P. Weber; *Macromolecules*, 28, 5686 (1995)). The tube and its contents were cooled at room temperature. The tube was opened under nitrogen and diphenylbutadiyne (404 mg, 2 mmol; available from Aldrich) was added. The solution was purged with nitrogen and the tube was sealed. The tube and its contents were heated at 135 ° C. overnight. The toluene solvent was removed by evaporation under reduced pressure. The residue was purified by column chromatography with silica gel and hexane/methylene chloride (4/1) as the eluent. In this way, 0.35 g, 86% yield, mp 219–220° C. was obtained. By DSC, Tg 177° C., Tm 220° C. $^1$H NMR δ: 7.61(dd, 4H, J=7.0 Hz), 7.43(m, 8H), 7.15(m, 20H), 7.05(d, 2H J=7.5 Hz), 7.02(d, 2H, J=7.5 Hz), 6.72(d, 2H, J=7.5 Hz), 6.64(d, 2H, J=7.5 Hz). $^{13}$C NMR δ: 146.49, 145.99, 143.65, 143.16, 139.79, 139.59, 139.47, 139.30, 131.47, 131.17, 130.69, 130.66, 130.47, 130.41, 128.28, 128.21, 128.17, 128.03, 127.99, 127.96, 127.65, 127.48, 127.39, 127.31, 127.21, 126.82, 126.80, 125.63, 125.30, 124.81, 123.50, 123.45, 123.24, 123.22, 123.19, 122.39, 98.58, 98.39, 97.34, 97.22, 88.97, 88.81, 88.27, 88.19. Forty-four carbon signals are observed. Structure IV should give rise to 48 carbons resonances. IR υ, 3056, 2920, 2211, 1951, 1883, 1804, 1755, 1669, 1597, 1490, 1442, 1406, 1275, 1175, 1070, 1026, 910, 841, 806, 754, 693 cm$^{-1}$ UV $\lambda_{max}$ nm(ε): 365(68000), 341(44000), 313(76000), 228(44000). Fluorescence $\lambda_{max}$ 392 nm in solution (quantum yield=16% ) or $\lambda_{max}$ 408 nm as a solid film when excited at 310–320 nm. The $\lambda_{max}$ of the excitation spectrum is 392 nm. By TGA, the tetramer is stable to 310° C. Above 310° C., a steady loss of weight occurs. By 650° C., 98% of the initial sample weight is lost. DSC: $T_g$ (glass transition)=177° C., Tm(melting point)= 220° C. MS: M$^+$(=molecular ion) Calc. for $(C_{16}H_{10})_4$808.3130 Found: 808.3159, the base peak corresponds to $(C_{16}H_{10})_3^+$.

Cyclic voltammetry in DMF showed a reduction potential of −1.59 V (vs. SCE)

V.A.5.b. Tetramer of di-p-tolylbutadiyne ("COT-Me")

Dihydridocarbonyltris(triphenylphosphine)ruthenium (110 mg, 120 μmol), toluene 3 mL, and styrene (13.6 μl, 120 μmol) were placed in an Ace pressure tube for activating as above. Di-p-tolylbutadiyne (1.0 g, 1.1 mmol) was added. The solution was purged again with nitrogen and the pressure tube was sealed. The tube and its contents were heated at 135° C. overnight. After reaction, the product was purified by column chromatography (silica ge/hexane/ethyl acetate) to give a yellow solid (0.70 g), yield 70%, mp 263–265° C. by DSC T$_m$=265° C., and Tg=214° C. $^1$H NMR δ: 7.61 (dd, 4H, J=8 Hz), 7.32(dd, 4H, J=8 M), 7.20(d, 2H, J=8 Hz), 7.15(dd, 4H, J=8 Hz), 7.08(m, 10H), 6.98(d, 2H, J=8 Hz), 6.95(d, 2H, J=8 Hz), 6.77(d, 2H, J=8 Hz), 6.69(d, 2H J=Hz), 2.50(s, 3H), 2.49(s, 3H), 2.34(s, 3H), 2.33(s, 3H), 2.32(s, 6H), 2.28(s, 3H), 2.27(s, 3H). In toluene-d$_8$ solvent, eight different methyl peaks were observed: 2.56, 2.55, 2.33, 2.32, 2.26, 2.24, 2.19, 2.17 ppm.

Off resonance $^{13}$C NMR δ: 146.10(t, $^3$J=3 Hz), 145.39(t, $^3$J=3 Hz), 143.45(t, $^3$J=3 Hz), 142.80(t, $^3$J=3 Hz), 138.26(t of q, $^2$J=8 Hz, $^3$J=2 Hz), 138.24(t of q, $^2$J=8 Hz, $^3$J=2 Hz), 13 7.98(t of q, $^2$J =8 Hz, $^3$J=2 Hz), 137.95(t of q, $^2$J=8 Hz, 3J=2 Hz), 136.97(t of q, 2J=8 Hz, 3J=2 Hz), 136.95(t of q, 2J=8 Hz, 3J=2 Hz), 136.90(t of q, 2J=8 Hz, 3J=2 Hz), 136.71 (t, 2J=7.5 Hz) 136.63 (t, 2J=7.5 Hz), 136.51 (t, 2J=7.5 Hz), 135.99(t of q, 2J=8 Hz, 3J=2 Hz), 131.32(d of d, V=163 Hz, 2J=6.5 M), 131.00(d of d, V=163 Hz, 2J=6.5 Hz), 130.56(d of d, 'J=163 Hz, 2J=6.5 Hz), 130.53(d of d, 'J=163 Hz, 2J=6.5 Hz), 130.40(d of d, 'J=163 Hz, 2J=6.5 Hz), 130.38(d of d, 'J=163Hz, 2J=6.5 Hz), 128.92(d of d,'J=163 Hz, 2J=6.5 Hz), 128.88(d of d,'J=163 Hz, 2J=6.5 Hz), 128.71(d of d, V=163 Hz, 2J=6.5 Hz), 128.68(d of d, V=163 Hz, 2J=6.5 Hz), 127.96(d of d, V=163 Hz, 2J=6.5 Hz), 127.91(d of d, V=163 Hz, 2J=6.5 Hz), 127.89(d of d, V=163 Hz, 2J=6.5 1U), 127.82(d of d, V=163 Hz, 2J=6.5 Hz), 125.67(s), 124.59(s), 123.28(s), 122.29(s), 120.59(t, 2J=8 Hz), 120.55 (t, 2J=8 Hz), 120.39(t, 2J=8 Hz), 120.34(t, 2J=8 Hz), 98.35 (t, 3J=5 Hz), 98.09(t, 3J=5 Hz), 97.06(t 3J=5 Hz), 96.91 (t 3J=5 Hz), 88.72(s), 88.70(s), 88.06(s), 87.99(s), 21.48(t of q, V=127 Hz, 3 J=5 Hz), 21.46(t of q, V=127 Hz, 3J=5 Hz), 21.41 (t of q, V=127 Hz, 3J=5 Hz), 21.24(t of q, V=127 Hz, 3J=5 Hz), 21.23(t of q, 127 Hz, 3J=5 Hz).

Fifty carbon resonances are observed. Structure IV should give rise to 56 carbon signals.

From the off resonance $^{13}$C NMR spectra, the eight signals due to acetylenic carbons can be divided into two groups. Four carbons are split to triplet, while the other four carbons are singlet. The four carbon triplets are due to long range three bond coupling by the two ortho aromatic protons adjacent to triple bond. The other four carbon singlets indicate that they are connected to the ipso carbon. This is consistent with four different p-tolylethynyl groups.

IR υ: 3026, 2920, 2860, 2209, 1904, 1611, 1511, 1446, 1415, 1215, 1178, 1112, 1021, 815, 758 cm$^{-1}$. UV $\lambda_{max}$ ($\epsilon$): 366(49800), 317(73000), 245(32600). Fluorescence $\lambda_{max}$ 402 nm (quantum yield=47%) when excited at 310–320 μm. The $\lambda_{max}$ of the excitation spectrum is 375 nm. TGA: The tetramer is stable until 360° C. Above this temperature, the material undergoes catastrophic decomposition. From 360 to 600° C., 97% of the initial sample weight is lost.

Cyclic voltammetry in DMF showed a reduction potential of –1.71 V.

V.A.5.c. Tetramer of di-p-methoxyphenylbutadiyne

Di-p-methoxyphenylbutadiyne was treated with activated ruthenium catalyst as above. After purification, the unsymmetrical cyclic tetramer was obtained in 29%, mp, 199–200° C. $^1$H NMR δ: 7.62(d, 2H, J=8.5 Hz), 7.61 (d, 2K J=8.5 Hz), 7.21 (d, 2FL J=8.5 Hz), 7.14(d, 4K J=8.5 Hz), 7.12(d, 21L J=8.5 Hz), 7.02(d, 2H, J=8.5 Hz), 7.01 (d, 21-L J=8.5 Hz), 6.84–6.64(m, 16H), 3.86(s, 3H), 3.85(s, 3H), 3.74(s, 3H), 3.73(s, 3H), 3.72(s, 6H), 3.69(s, 3H), 3.68 (s, 3M. $^{13}$C NMR δ: 159.61, 159.42, 159.08, 158.22, 145.16, 144.64, 142.84, 142.27, 132.91, 132.61, 132.48, 132.38, 132.27, 132.22, 132.14, 132.07, 131.98, 131.92, 131.90, 131.84, 128.53, 128.43, 125.58, 124.68, 123.41, 122.51, 115.87, 115.84, 115.65, 115.62, 113.91, 113.89, 113.71, 113.70, 112.73, 112.67, 112.64, 98.14, 97.91, 86.90, 96.76, 88.26, 88.23, 87.57, 87.52, 55.45, 55.43, 55.29, 55.28, 55.26, 55.23, 55.20, 55.18. Fifty-three carbon resonances are observed. The unsymmetrical cyclic tetramer should give rise to fifty-six signals. IR: 2952, 2921, 2850, 2207, 1730, 1606, 1511, 1463, 1437, 1417, 1290, 1251, 1170, 1106, 1029, 830, 774 cm$^{-1}$ UV $\lambda_{max}$ nm($\epsilon$) 365 (50000) 325–399 (65000): Fluorescence $\lambda_{max}$ 412 nm (quantum yield=79%) when excited at 310–320 nm. The $\lambda_{max}$ of the excitation spectrum is 375 nm. By DSC, Tg 194° C., Tm 200° C. TGA: The tetramer is stable until 335° C. Above this temperature, the material undergoes catastrophic decomposition. From 335° C. to 566° C., 94% of the initial sample weight was lost.

V.A.5.d. Synthesis of tetramer of bis-(β-naphthyl)-1,4-butadiyne

Dihydridocarbonyltristriphenylphosphine (27.54 mg, 30 μmol), toluene 2 mL, and styrene (3.4 μl, 30 μmol) were placed in an Ace pressure tube. The tube and its contents were purged with nitrogen for a few minutes. The tube was sealed and heated at 110° C. until the color changed to orange. It was cooled to room temperature, bis-(β-naphthyl)-1,4-butadiyne(0.302 g, 1 mmol) was added to the tube. It was purged with nitrogen, and sealed. The tube and its contents were heated at 135° C. overnight. After removing the toluene by evaporation, the residue was purified by column chromatography. In this way, 0.1 g, 33% yield was obtained. Eight acetylenic carbons in $^{13}$C NMR were observed. δ: 99.58, 99.48, 98.33, 98.23, 89.66, 89.51, 88.94, 88.92. respectively.

V.A.5.e. Synthesis of tetramer of bis(3-thienyl)-1,4-butadiyne

The catalyst was activated as above. bis(3-Thienyl)-1,4-butadiyne (0.214 g, 1 mmol) was added to the tube. It was purged with nitrogen, and sealed. The tube and its contents were heated at 135° C. overnight. After removing the toluene by evaporation, the residue was purified by column chromatography. In this way, 0.12 g, 56% yield was obtained. $^1$H NMR: δ: 7.70(s, 1H) 7.67(s, 1H), 7.51(d, 1H, J=1.5 Hz), 7.48(d, 1H, J=1.5 Hz), 7.42(m, 2H), 7.37(s, 1H), 7.32(s, 1H), 7.27(3H, m), 7.20(5H, m), 7.11(s, 1H), 7.08(s, 1H, J=1.5 Hz), 6.99(d, 1H, J=1.5 Hz), 6.95(d, 2H, J=1.5 Hz), 6.79(d, 1H, J=1.5 Hz), 6.74(d, 1H, J=1.5 Hz).

Eight acetylenic carbons in $^{13}$C NMR were observed. δ: 93.61, 93.48, 92.6, 92.52, 88.31, 88.20, 87.71, 87.63, respectively. By TGA, this material is stable to 310° C., from 310° C. to 640° C., 97% of the initial weight is steadily lost.

Cyclic voltammetry in DMF showed a reduction potential of –1.68 V.

V.A.5.f. Synthesis of tetramer of bis-(4-trifluoromethylphenyl)-1,4-butadiyne

The catalyst was activated as above. bis-(4-Trifluorumethylphenyl)-1,4-butadiyne (0.338 g, 1 mmol) was added to the tube. It was purged with nitrogen, and sealed. The tube and its contents were heated at 135° C. overnight. After removing the toluene by evaporation, the residue was purified by column chromatography. In this way, 0.1 g, 29% yield was obtained. $^1$H NMR δ: 7.83(d, 2H, J=8 Hz), 7.77(d, 2H, J=8 Hz), 7.59(m, 14 H), 7.37(dd, 8H, J=8 Hz), 7.25(d, 2H, J=8 Hz), 7.14(d, 2H, J=8 Hz), 6.68(d, 2H, J=8 Hz). Eight acetylenic carbons in $^{13}$C NMR were observed. δ: 98.59, 98.56, 97.25, 89.51, 89.09, 88.80, 80.96, 75.62, respectively.

V.B.1. Device preparation

The device structure that we chose to use is very similar to the standard vacuum deposited one (FIG. 1). A hole transporting layer ("HTL") is first deposited onto the ITO coated glass substrate. For all of the devices described here, the HTL consisted of 400 Å of NPD. Onto the NPD a thin film of the cyclooctatetraene derivative is deposited. Two different derivatives ("COTs") were examined (FIG. 2), each at two different film thicknesses (which were 400 and 200 Å). The device is finished by depositing a Mg—Ag electrode onto the COT film. All of the depositions were carried out at a vacuum less than 5×10–5 Torr. The devices were tested in air, without packaging.

COTs themselves have high fluorescence yields and might be suitable as blue emitting host materials (FIG. 2). However, in the embodiments discussed below, the NPD is functioning as the emissive molecule.

V.B.2. First Example

The OLED of the first device comprises an ETL comprising COT-Me. The standard undoped device gives an IV characteristic (FIG. 3) that is very similar to an analogous device made with an electron transporting layer of Alq3 with a blue emitter.

The spectra of the OLED of the first example are consistent with emission from the NPD of the hole transporting layer, and are not consistent with emission from the COT-Me of the electron transporting layer. The EL spectrum is identical to the photoluminescence and electroluminescence spectra of NPD.

This result is not surprising since the energy of an exciton in COT-Me wold be greater than that of one in NPD. The excitons are formed at or near the NPD/COT-Me interface and are trapped in the lower energy NPD layer.

V.B.3. Second Example

A similar result is observed for an OLED comprising an ETL comprising COT-H. In FIG. 4, the IV curve is shifted to somewhat higher bias, but the emission is exclusively from the NPD layer.

The quantum yields for the COT-Me and COT-H are 0.15 and 0.05 respectively. These efficiencies are consistent with other devices wherein a blocking layer is added to force emission from the NPD layer. If the COT layer is thinned down, the current-voltage characteristic shifts to lower bias at a given current level (FIG. 5); however, the quantum yield for the device drops. The exact layer thickness for the best quantum efficiency and lowest turn-on voltage could be optimized without undue experimentation.

V.B.4. Third and Fourth Examples

To confirm that the NPD is the site of the emission, another device was fabricated with a perylene dopant in the NPD layer. The shift in energy relative to the photoluminescence spectra of the COT derivative could have been due to microcavity effects. The perylene will efficiently trap excitons in NPD and will emit with a distinctly different spectrum. If microcavity effects are responsible for the emission at 435 nm, the perylene doping will have little effect on the EL spectrum.

The EL spectra for perylene-doped NPD devices prepared with both COT-Me (Example 3) and COT-H (Example 4) are shown in FIGS. 6 and 7 respectively.

Each spectrum is clearly due to perylene, confirming that the site of the emission is in the NPD. As expected, the doping leads to an increase in the measured quantum yields to 0.6 (for COT-Me OLED) and to 0.14 (for COT-H OLED). The IV characteristics of these devices are unchanged relative to the undoped devices.

V.B.5. Fifth Example

As a double check of the proposal that the emission is completely centered in the NPD layer, we prepared a device with perylene coped into the COT-Me layer. The COT-Me doped device was 400 Å of NPD and 400 Å of 1% perylene doped COT-Me. The current-voltage curve and EL spectra are shown in FIG. 8. The emission is exactly the same as the for the undoped device, with roughly the same quantum efficiency, i.e., pure NPD emission, demonstrating that excitons have been confined to the HTL layer.

Results of Examples 1–5

The use of the materials of this invention may make it possible to eliminate the hole and/or exciton blocking layer used to prepare HTL emitting OLEDs. The COTs represent a new class of wide gap electron transporters that are readily deposited in vacuum. They can be synthesized in good yield (>75% isolated yields) from commercially available starting materials.

We are studying a range of cathode materials to see if Mg is necessary or if other less reactive metals an be used for the novel COT materials. We are also exploring the use of the material with phosphorescent dye doped HTLs for blue, green and red OLEDs. The use of COT derivatives, as opposed to Alq3 materials, is especially significant because the energy gap in COT derivatives is large enough to allow efficient energy transfer to blue emissive dopants as well as green and red. The magnitude of the gap is known from the emission at 390 to 410 nm which is reported herein and not previously known.

V. C. Other Molecular Depictions

A molecule for the hole-transporting layer of the invention is depicted below.

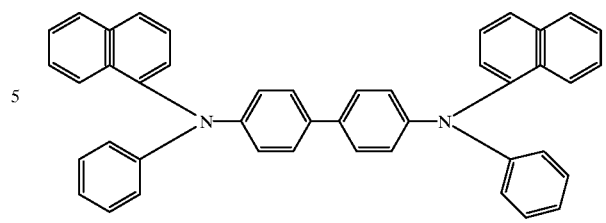

The invention will work with other hole-transporting molecules known by one of ordinary skill to work in hole transporting layers of OLEDs.

A molecule which could be used as the host in the emissive layer of the invention is depicted below.

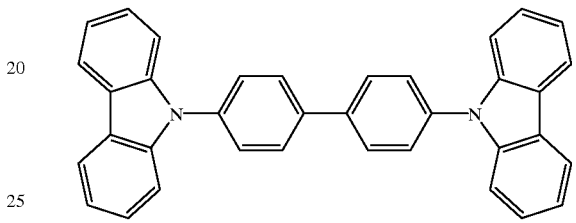

The invention will work with other molecules known by one of ordinary skill to work as hosts of emissive layers of OLEDs. For example, the host material could be a hole-transporting matrix and could be selected from the group consisting of substituted tri-aryl amines and polyvinylcarbazoles.

FIGS. 10 through 19 give additional data on the molecules of this invention.

V.D. Uses of Device

The OLED of the present invention may be used in substantially any type of device which is comprised of an OLED, for example, in OLEDs that are incorporated into a larger display, a vehicle, a computer, a television, a printer, a large area wall, theater or stadium screen, a billboard or a sign.

The present invention as disclosed herein may be used in conjunction with co-pending applications: "High Reliability, High Efficiency, Integratable Organic Light Emitting Devices and Methods of Producing Same", Ser. No. 08/774, 119 (filed Dec. 23, 1996); "Novel Materials for Multicolor Light Emitting Diodes", Ser. No. 08/850,264 (filed May 2, 1997); "Electron Transporting and Light Emitting Layers Based on Organic Free Radicals", Ser. No. 08/774,120 (filed Dec. 23, 1996)(issued as U.S. Pat. No. 5,811,833 on Sept. 22, 1998); "Multicolor Display Devices", Ser. No. 08/772, 333 (filed Dec. 23, 1996); "Red-Emitting Organic Light Emitting Devices (OLED's)", Ser. No. 08/774,087 (filed Dec. 23, 1996); "Driving Circuit For Stacked Organic Light Emitting Devices", Ser. No. 08/792,050 (filed Feb. 3, 1997) (issued as U.S. Pat. No. 5,757,139 on May 26, 1998); "High Efficiency Organic Light Emitting Device Structures", Ser. No. 08/772,332 (filed Dec. 23, 1996)(issued as U.S. Pat. No. 5,834,893 on Nov. 10, 1998); "Vacuum Deposited, Non-Polymeric Flexible Organic Light Emitting Devices", Ser. No. 08/789,319 (filed Jan. 23, 1997)(issued as U.S. Pat. No. 5,844,363 on Dec. 1, 1998); "Displays Having Mesa Pixel Configuration", Ser. No. 08/794,595 (filed Feb. 3, 1997); "Stacked Organic Light Emitting Devices", Ser. No. 08/792, 046 (filed Feb. 3, 1997)(issued as U.S. Pat. No. 5,917,280 on Jun. 29, 1999); "High Contrast Transparent Organic Light Emitting Devices", Ser. No. 08/792,046 (filed Feb. 3, 1997); "High Contrast Transparent Organic Light Emitting Device Display", Ser. No. 08/821,380 (filed Mar. 20, 1997); "Organic Light Emitting Devices Containing A Metal Complex of 5-Hydroxy-Quinoxaline as A Host Material", Ser. No. 08/838,099 (filed Apr. 15, 1997)(issued as U.S. Pat. No. 5,861,219 on Jan. 19, 1999); "Light Emitting Devices Having High Brightness", Ser. No. 08/844,353 (filed Apr. 18, 1997); "Organic Semiconductor Laser", Ser. No. 08/859,468 (filed May 19, 1997); "Saturated Full Color Stacked Organic Light Emitting Devices", Ser. No. 08/858,994 (filed on May 20, 1997)(issued as U.S. Pat. No. 5,932,895 on Aug. 3, 1999); "Plasma Treatment of Conductive Layers", PCT/US97/10252, (filed Jun. 12, 1997); "Novel Materials for Multicolor Light Emitting Diodes", Ser. No. 08/814,976, (filed Mar. 11, 1997); "Novel Materials for Multicolor Light Emitting Diodes", Ser. No. 08/771,815, (filed Dec. 23, 1996); "Patterning of Thin Films for the Fabrication of Organic Multi-color Displays", PCT/US97/10289, (filed Jun. 12, 1997), and "Double Heterostructure Infrared and Vertical Cavity Surface Emitting Organic Lasers", PCT/US98/09480 filed May 8, 1998; U.S. Pat. No. 5,874,803 issued Feb. 23, 1999; U.S. Pat. No. 5,707,745 issued Jan. 13, 1998; U.S. Pat. No. 5,703,436 issued Dec. 30, 1997; and U.S. Pat. No. 5,757,026 issued May 26, 1998 each co-pending application or patent being incorporated herein by reference in its entirety.

What is claimed:

1. A cyclooctatetraene compound having a chemical structure as represented by the formula selected from the group consisting of:

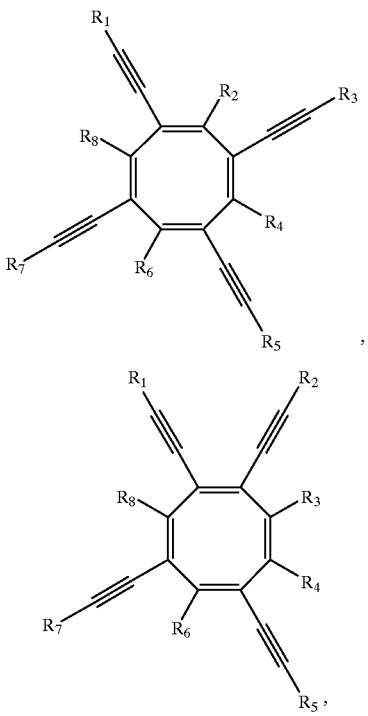

-continued

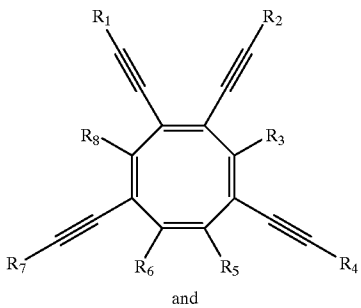

and

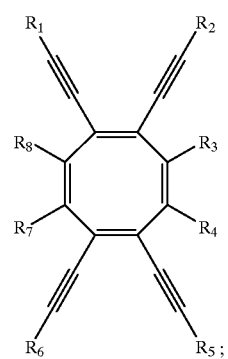

wherein $R_1$, $R_2$, $R_3$, $R_4$, $R_5$, $R_6$, $R_7$ and $R_8$ are selected from the group consisting of phenyl, naphthyl, thienyl, benzthienyl, quinolinyl and pyridyl, each of which may be unsubstituted or substituted with at least one of lower alkyl, lower alkoxy, trifluoromethyl, halogen, nitro, CN, carbonyl and lower alkyl ester.

2. The cyclooctatetraene compound of claim 1, wherein $R_1$, $R_2$, $R_3$, $R_4$, $R_5$, $R_6$, $R_7$ and $R_8$ are selected from the group consisting of unsubstituted phenyl and substituted phenyl.

3. The cyclooctatetraene compound of claim 2, wherein $R_1$, $R_2$, $R_3$, $R_4$, $R_5$, $R_6$, $R_7$ and $R_8$ are unsubstituted phenyl.

4. The cyclooctatetraene compound of claim 2, wherein $R_1$, $R_2$, $R_3$, $R_4$, $R_5$, $R_6$, $R_7$ and $R_8$ are monosubstituted phenyl.

5. The cyclooctatetraene compound of claim 4, wherein the monosubstituted phenyl is monosubstituted with a methyl.

6. The cyclooctatetraene compound of claim 5, wherein the methyl is in the para-position.

7. The cyclooctatetraene compound of claim 4, wherein the monosubstituted phenyl is monosubstituted with a methoxy.

8. The cyclooctatetraene compound of claim 4, wherein the monosubstituted phenyl is monosubstituted with a trifluoromethyl.

9. The cyclooctatetraene compound of claim 1, wherein $R_1$, $R_2$, $R_3$, $R_4$, $R_5$, $R_6$, $R_7$ and $R_8$ are selected from the group consisting of unsubstituted naphthyl and substituted naphthyl.

10. The cyclooctatetraene compound of claim 9, wherein $R_1$, $R_2$, $R_3$, $R_4$, $R_5$, $R_6$, $R_7$ and $R_8$ are selected from the group consisting of unsubstituted β-naphthyl and substituted β-naphthyl.

11. The cyclooctatetraene compound of claim 9, wherein $R_1$, $R_2$, $R_3$, $R_4$, $R_5$, $R_6$, $R_7$ and $R_8$ are unsubstituted naphthyl.

12. The cyclooctatetraene compound of claim 1, wherein $R_1$, $R_2$, $R_3$, $R_4$, $R_5$, $R_6$, $R_7$ and $R_8$ are selected from the group consisting of unsubstituted thienyl and substituted thienyl.

13. The cyclooctatetraene compound of claim 12, wherein $R_1, R_2, R_3, R_4, R_5, R_6, R_7$ and $R_8$ are selected from the group consisting of unsubstituted 3-thienyl and substituted 3-thienyl.

14. The cyclooctatetraene compound of claim 1, wherein $R_1, R_2, R_3, R_4, R_5, R_6, R_7$ and $R_8$ are selected from the group consisting of unsubstituted pyridyl and substituted pyridyl.

15. The cyclooctatetraene compound of claim 1, wherein $R_1, R_2, R_3, R_4, R_5, R_6, R_7$ and $R_8$ are selected from the group consisting of unsubstituted quinolinyl and substituted quinolinyl.

16. The cyclooctatetraene compound of claim 1, wherein $R_1, R_2, R_3, R_4, R_5, R_6, R_7$ and $R_8$ are selected from the group consisting of unsubstituted benzthienyl and substituted benzthienyl.

17. A cyclooctatetraene compound having a chemical structure as represented by the formula selected from the group consisting of:

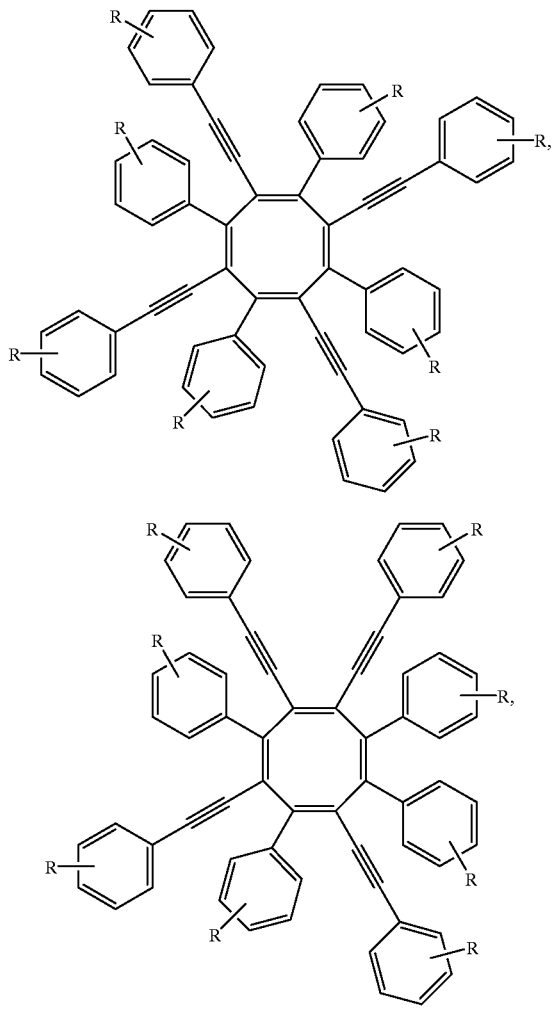

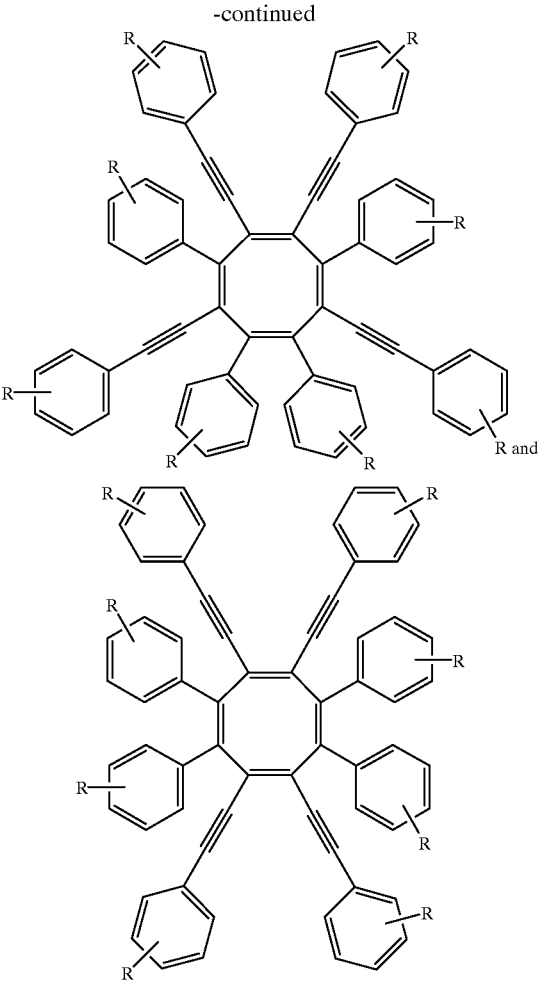

wherein R is selected from the group consisting of a hydrogen, lower alkyl, lower alkoxy, trifluoromethyl, halogen, nitro, CN, carbonyl and lower alkyl ester.

18. The cyclooctatetraene compound of claim 17, wherein R is a lower alkyl.

19. The cyclooctatetraene compound of claim 18, wherein the lower alkyl is a methyl.

20. The cyclooctatetraene compound of claim 19, wherein the methyl is in the para-position.

21. The cyclooctatetraene compound of claim 17, wherein R is a hydrogen.

22. The cyclooctatetraene compound of claim 17, wherein R is a lower alkoxy.

23. The cyclooctatetraene compound of claim 22, wherein the lower alkoxy is a methoxy.

24. The cyclooctatetracne compound of claim 17, wherein R is a trifluoromethyl.

25. The cyclooctatetraene compound of claim 17, wherein R is a halogen.

26. The cyclooctatetraene compound of claim 17, wherein R is a nitro.

27. A cyclooctatetraene derivative formed as a tetramer of a single monomer wherein the monomer is selected from the group consisting of diphenylbutadiyne, di-p-tolylbutadiyne, di-p-methoxyphenylbutadiyne, bis-(b-naphthyl)butadiyne, bis(3-thienyl)butadiyne and bis(4-trifluoromethylphenyl)butadiyne.

* * * * *

UNITED STATES PATENT AND TRADEMARK OFFICE
CERTIFICATE OF CORRECTION

PATENT NO. : 6,350,875 B1
DATED : February 26, 2002
INVENTOR(S) : Weber et al.

It is certified that error appears in the above-identified patent and that said Letters Patent is hereby corrected as shown below:

Column 5,
Line 55, change "phosphore-cence" to -- phosphorescence --;

Column 8,
Line 1, change "rear" to -- near --;
Line 52, change "cyclooctatetracnes" to -- cyclooctatetraenes --;

Column 9,
Line 49, change "COT-CH30" to -- COT-CH3O --;

Column 10,
Line 13, below molecular structural diagrams and above line 14 insert: -- R=aryl, alkyl, alkynyl or silyl group --;
Line 28, below molecular structural diagrams and above line 29 insert: -- R=aryl, alkyl, alkynyl or silyl group --;

Column 11,
Line 15, change "member" to -- members --;

Column 12,
Line 60, change "Lu" to -- to --;

Column 14,
Line 38, change "Methoxypbenylethynyl" to -- Methoxyphenylethynyl --;

Column 18,
Line 8, after "1H" (first occurrence), insert -- ), 7.04(d,1H --;
Line 19, change "Trifluorumethylphenyl" to -- Trifluoromethylphenyl --; and

UNITED STATES PATENT AND TRADEMARK OFFICE
CERTIFICATE OF CORRECTION

PATENT NO. : 6,350,875 B1
DATED : February 26, 2002
INVENTOR(S) : Weber et al.

It is certified that error appears in the above-identified patent and that said Letters Patent is hereby corrected as shown below:

Column 24,
Line 60, change "cyclooctatetracne" to -- cyclooctatetraene --.

Signed and Sealed this

Nineteenth Day of November, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO.       : 6,350,875 B1
APPLICATION NO.  : 09/816527
DATED            : February 26, 2002
INVENTOR(S)      : William Weber et al.

It is certified that error appears in the above-identified patent and that said Letters Patent is hereby corrected as shown below:

Column 1, line 5 (after the title) please insert the following paragraph:

<u>GOVERNMENT RIGHTS</u>
This invention was made with Government support under Contract No. F49620-96-1-00035 awarded by the Air Force Office of Scientific Research and Contract No.: CHE9616796 awarded by the National Science Foundation. The government has certain rights in this invention.

Signed and Sealed this

Twenty-ninth Day of January, 2008

JON W. DUDAS
*Director of the United States Patent and Trademark Office*